(12) United States Patent
Hassidov et al.

(10) Patent No.: US 10,881,277 B2
(45) Date of Patent: Jan. 5, 2021

(54) DISTAL FRONT END FOR COORDINATED POSITIONING OF AN ENDOSCOPE WITH A SUCTION DEVICE

(71) Applicant: Motus GI Medical Technologies Ltd., Tirat HaCarmel (IL)

(72) Inventors: Noam Hassidov, Moshav Bustan MaGalil (IL); Boris Shtul, Moshav Zerufa (IL); Eyal Kochavi, Haifa (IL); Tzach Arnon, Yodfat (IL); Kobi Luleko, Eshchar (IL); Dan Blecher, Ramat-Gan (IL)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 0 days.

(21) Appl. No.: 14/722,400

(22) Filed: May 27, 2015

(65) Prior Publication Data

US 2015/0257633 A1 Sep. 17, 2015

Related U.S. Application Data

(63) Continuation-in-part of application No. PCT/IL2014/051014, filed on Nov. 20, 2014.
(Continued)

(51) Int. Cl.
*A61B 1/00* (2006.01)
*A61B 1/31* (2006.01)
*A61B 1/015* (2006.01)

(52) U.S. Cl.
CPC .......... *A61B 1/0014* (2013.01); *A61B 1/0008* (2013.01); *A61B 1/00089* (2013.01);
(Continued)

(58) Field of Classification Search
CPC .............. A61B 1/0008; A61B 1/00089; A61B 1/00091; A61B 1/00094; A61B 1/00101; A61B 1/00112; A61B 1/00114; A61B 1/00117; A61B 1/00119; A61B 1/00121; A61B 1/00124; A61B 1/00126;
(Continued)

(56) References Cited

U.S. PATENT DOCUMENTS 4,270,525 A 6/1981 Furihata
4,526,622 A 7/1985 Takamura et al.
(Continued)

FOREIGN PATENT DOCUMENTS

CN 101301191 11/2008
CN 102046064 5/2011
(Continued)

OTHER PUBLICATIONS

Communication Relating to the Results of the Partial International Search dated Feb. 24, 2015 From the International Searching Authority Re. Application No. PCT/IL2014/051014.
(Continued)

*Primary Examiner* — Ryan N Henderson

(57) ABSTRACT

Devices for joining an endoscope with a system for cleaning a colon or other body lumen are presented. Embodiments include variable placement of distal portions of suction components with respect to the endoscope, multiple suction tubes and/or suction portals, and devices for protecting colon walls from suction damage.

15 Claims, 23 Drawing Sheets

Related U.S. Application Data

(60) Provisional application No. 62/012,997, filed on Jun. 17, 2014, provisional application No. 61/906,982, filed on Nov. 21, 2013.

(52) U.S. Cl.
CPC ...... *A61B 1/00094* (2013.01); *A61B 1/00101* (2013.01); *A61B 1/00128* (2013.01); *A61B 1/015* (2013.01); *A61B 1/31* (2013.01)

(58) Field of Classification Search
CPC ............ A61B 1/00128; A61B 1/00135; A61B 1/00142; A61B 1/00137; A61B 1/0014; A61B 1/00154
USPC ................ 600/104, 106, 114, 115, 127–130, 600/156–159, 175
See application file for complete search history.

(56) References Cited

U.S. PATENT DOCUMENTS

| | | | |
|---|---|---|---|
| 5,096,385 A | 3/1992 | Georgi et al. | |
| 5,201,908 A * | 4/1993 | Jones | A61B 1/00091 600/123 |
| 5,279,542 A | 1/1994 | Wilk | |
| 5,545,121 A | 8/1996 | Yabe et al. | |
| 5,554,098 A | 9/1996 | Yabe et al. | |
| 5,630,795 A | 5/1997 | Kuramoto et al. | |
| 5,674,182 A | 10/1997 | Suzuki et al. | |
| 5,679,110 A | 10/1997 | Hamazaki | |
| 5,725,476 A | 3/1998 | Yasui et al. | |
| 5,725,477 A * | 3/1998 | Yasui | A61B 1/00091 600/121 |
| 5,788,650 A | 8/1998 | Dotolo | |
| 5,924,977 A | 7/1999 | Yabe et al. | |
| 6,309,346 B1 | 10/2001 | Farhadi | |
| 6,409,657 B1 * | 6/2002 | Kawano | A61B 1/00091 600/127 |
| 6,641,553 B1 | 11/2003 | Chee et al. | |
| 6,786,864 B2 * | 9/2004 | Matsuura | A61B 1/0008 600/104 |
| D536,449 S | 2/2007 | Nakajima et al. | |
| 2001/0053909 A1 * | 12/2001 | Nakada | A61B 1/00089 606/47 |
| 2004/0127891 A1 | 7/2004 | Humble et al. | |
| 2005/0033264 A1 | 2/2005 | Redinger | |
| 2005/0154262 A1 | 7/2005 | Banik et al. | |
| 2005/0256464 A1 | 11/2005 | Pallas | |
| 2006/0025729 A1 | 2/2006 | Leiboff et al. | |
| 2006/0069304 A1 * | 3/2006 | Takemoto | A61B 1/00087 600/104 |
| 2006/0079861 A1 | 4/2006 | Matasov | |
| 2006/0235458 A1 | 10/2006 | Belson | |
| 2006/0270906 A1 * | 11/2006 | Matsuno | A61B 1/12 600/156 |
| 2007/0015965 A1 | 1/2007 | Cox et al. | |
| 2007/0234716 A1 | 10/2007 | Hirooka | |
| 2008/0188715 A1 * | 8/2008 | Fujimoto | A61B 1/00091 600/157 |
| 2009/0143722 A1 | 6/2009 | Kim | |
| 2009/0198212 A1 | 8/2009 | Timberlake et al. | |
| 2009/0292172 A1 | 11/2009 | Roskopf et al. | |
| 2010/0025644 A1 | 2/2010 | Jockisch | |
| 2010/0063358 A1 | 3/2010 | Kessler | |
| 2010/0076420 A1 * | 3/2010 | Carter | A61B 1/12 606/21 |
| 2010/0185056 A1 | 7/2010 | Gordon et al. | |
| 2010/0185150 A1 | 7/2010 | Zacharias | |
| 2010/0256447 A1 | 10/2010 | Dubi et al. | |
| 2010/0298773 A1 | 11/2010 | Nitsan et al. | |
| 2011/0034865 A1 | 2/2011 | Wallace | |
| 2011/0092892 A1 | 4/2011 | Nitsan et al. | |
| 2011/0105845 A1 | 5/2011 | Gordon et al. | |
| 2012/0101336 A1 * | 4/2012 | Hirsch | A61B 1/00135 600/156 |
| 2012/0289910 A1 | 11/2012 | Shtul et al. | |
| 2013/0046138 A1 * | 2/2013 | McLawhorn | A61B 1/00101 600/104 |
| 2013/0085442 A1 | 4/2013 | Shtul et al. | |
| 2013/0131453 A1 | 5/2013 | Imai | |
| 2013/0296771 A1 | 11/2013 | Shtul et al. | |
| 2013/0331855 A1 | 12/2013 | Smith et al. | |
| 2016/0206805 A1 | 7/2016 | Hassidov et al. | |
| 2016/0317000 A1 | 11/2016 | Hassidov et al. | |
| 2016/0324412 A1 | 11/2016 | Hassidov et al. | |
| 2017/0173256 A1 | 6/2017 | Hassidov et al. | |
| 2018/0020905 A1 | 1/2018 | Chouinard et al. | |
| 2018/0235448 A1 | 8/2018 | Hassidov et al. | |
| 2019/0247566 A1 | 8/2019 | Hassidov et al. | |
| 2019/0298910 A1 | 10/2019 | Hassidov et al. | |

FOREIGN PATENT DOCUMENTS

| | | |
|---|---|---|
| CN | 102076271 | 5/2011 |
| CN | 102137615 | 7/2011 |
| CN | 102711590 | 10/2012 |
| CN | 102892445 | 1/2013 |
| DE | 3624428 | 1/1988 |
| EP | 1284120 | 2/2003 |
| EP | 1284128 | 2/2003 |
| EP | 1508294 | 2/2005 |
| EP | 2417896 | 2/2012 |
| JP | 50-81088 | 11/1973 |
| JP | 59-183202 | 12/1984 |
| JP | 05-161711 | 6/1993 |
| JP | 06-237887 | 8/1994 |
| JP | 06-066605 | 9/1994 |
| JP | 07-136103 | 5/1995 |
| JP | 07-155283 | 6/1995 |
| JP | 07-178040 | 7/1995 |
| JP | 11-216104 | 8/1999 |
| JP | 11-335405 | 12/1999 |
| JP | 2000-014767 | 1/2000 |
| JP | 2001-061760 | 3/2001 |
| JP | 2003-265595 | 9/2003 |
| JP | 2004-008822 | 1/2004 |
| JP | 2004-129951 | 4/2004 |
| JP | 2004-357846 | 12/2004 |
| JP | 2005-095582 | 4/2005 |
| JP | 2005-137423 | 6/2005 |
| JP | 2006-325816 | 12/2006 |
| JP | 2007-278191 | 10/2007 |
| JP | 2007-536073 | 12/2007 |
| JP | 2008-532727 | 8/2008 |
| JP | 2008-206559 | 9/2008 |
| JP | 2011-083329 | 4/2011 |
| JP | 2011-518584 | 6/2011 |
| JP | 2011-520567 | 7/2011 |
| JP | 2013-516300 | 5/2013 |
| JP | 2013-532023 | 8/2013 |
| JP | 2014-018563 | 2/2014 |
| JP | WO 2012/141261 | 7/2014 |
| WO | WO 92/17219 | 10/1992 |
| WO | WO 99/60934 | 12/1999 |
| WO | WO 00/54653 | 9/2000 |
| WO | WO 01/12102 | 2/2001 |
| WO | WO 2005/110580 | 11/2005 |
| WO | WO 2005/117685 | 12/2005 |
| WO | WO 2006/039511 | 4/2006 |
| WO | WO 2006/101908 | 9/2006 |
| WO | WO 2008/093288 | 8/2008 |
| WO | WO 2008/155776 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/138521 | 12/2010 |
| WO | WO 2011/083450 | 7/2011 |
| WO | WO 2011/083451 | 7/2011 |
| WO | WO 2011/158232 | 12/2011 |
| WO | WO 2015/029039 | 3/2015 |
| WO | WO 2015/075721 | 5/2015 |

(56) References Cited

FOREIGN PATENT DOCUMENTS

| WO | WO 2015/155776 | 10/2015 |
|---|---|---|
| WO | WO 2015/193896 | 12/2015 |
| WO | WO 2016/189533 | 12/2016 |
| WO | WO 2020/035868 | 2/2020 |

OTHER PUBLICATIONS

International Search Report and the Written Opinion dated May 6, 2015 From the International Searching Authority Re. Application No. PCT/IL2014/051014.
International Search Report and the Written Opinion dated Dec. 8, 2014 From the International Searching Authority Re. Application No. PCT/IL2014/050778.
Restriction Official Action dated Mar. 29, 2017 From the US Patent and Trademark Office Re. U.S. Appl. No. 15/108,601. (10 Pages).
International Preliminary Report on Patentability dated Dec. 29, 2016 From the International Bureau of WIPO Re. Application No. PCT/IL2015/050615. (8 Pages).
International Preliminary Report on Patentability dated Oct. 20, 2016 From the International Bureau of WIPO Re. Application No. PCT/IL2015/050379. (9 Pages).
International Search Report and the Written Opinion dated Sep. 11, 2016 From the International Searching Authority Re. Application No. PCT/IL2016/050544.
International Search Report and the Written Opinion dated Oct. 13, 2015 From the International Searching Authority Re. Application No. PCT/IL2015/050615.
International Search Report and the Written Opinion dated Oct. 16, 2015 From the International Searching Authority Re. Application No. PCT/IL2015/050379.
Ambrose et al. "Physiological Consequences of Orthograde Lavage Bowel Preparation for Elective Colorectal Surgery: A Review", Journal of the Royal Society of Medicine, 76(9): 767-771, Sep. 1983.
Invitation to Pay Additional Fees dated Aug. 12, 2015 From the International Searching Authority Re. Application No. PCT/IL2015/050379.
Translation of Notice of Grounds of Rejection dated Jan. 31, 2017 From the Japan Patent Office Re. Application No. 2016-553662. (4 Pages).
Notice of Reason for Rejection dated Jan. 31, 2017 From the Japan Patent Office Re. Application No. 2016-553662. (3 Pages).
International Search Report and the Written Opinion dated Feb. 16, 2016 From the International Searching Authority Re. Application No. PCT/IL2015/050379.
International Preliminary Report on Patentability dated Jun. 2, 2016 From the International Bureau of WIPO Re. Application No. PCT/IL2014/051014.
Communication Pursuant to Article 94(3) EPC dated Jan. 3, 2017 From the European Patent Office Re. Application No. 15735746.8. (4 Pages).
International Preliminary Report on Patentability dated Mar. 10, 2016 From the International Bureau of WIPO Re. Application No. PCT/IL2014/050778.
Official Action dated May 31, 2017 From the US Patent and Trademark Office Re. U.S. Appl. No. 15/108,601. (46 Pages).
Notice of Reason for Rejection dated Jun. 27, 2017 From the Japan Patent Office Re. Application No. 2016-553662. (3 Pages).
Applicant-Initiated Interview Summary dated Sep. 14, 2017 From the US Patent and Trademark Office Re. U.S. Appl. No. 15/108,601. (3 pages).
Translation of Notice of Grounds of Rejection dated Jun. 27, 2017 From the Japan Patent Office Re. Application No. 2016-553662. (3 Pages).
Official Action dated Oct. 19, 2017 From the US Patent and Trademark Office Re. U.S. Appl. No. 15/108,601. (38 pages).
Notice of Reasons for Rejection dated Feb. 6, 2019 From the Japan Patent Office Re. Application No. 2016-559518 and Its Translation Into English. (12 Pages).
Notice of Allowance dated Dec. 5, 2018 From the US Patent and Trademark Office Re. U.S. Appl. No. 14/915,266. (18 pages).
European Seach Report and the European Search Opinion dated Mar. 23, 2018 From the European Patent Office Re. Application No. 17196947.0. (7 Pages).
Communication Pursuant to Article 94(3) EPC dated Apr. 4, 2018 From the European Patent Office Re. Application No. 14816424.7. (5 Pages).
Notice of Reasons for Rejection dated Jul. 10, 2018 From the Japan Patent Office Re. Application No. 2016-537600 and Its Summary in English. (9 Pages).
Notice of Grounds of Rejection dated Sep. 5, 2018 From the Japan Patent Office Re. Application No. 2016-528831. (6 Pages).
Restriction Official Action dated Oct. 4, 2018 From the US Patent and Trademark Office Re. U.S. Appl. No. 15/959,397. (10 pages).
Translation dated Sep. 20, 2018 of Notice of Grounds of Rejection dated Sep. 5, 2018 From the Japan Patent Office Re. Application No. 2016-528831. (7 Pages).
Notice of Grounds of Rejection dated Nov. 6, 2018 From the Japan Patent Office Re. Application No. 2017-227752. (2 Pages).
Translation dated Nov. 14, 2018 of Notice of Grounds of Rejection dated Nov. 6, 2018 From the Japan Patent Office Re. Application No. 2017-227752. (2 Pages).
International Preliminary Report on Patentability dated Dec. 7, 2017 From the International Bureau of WIPO Re. Application No. PCT/IL2016/050544. (8 Pages).
Notification of Office Action and Search Report dated Nov. 16, 2017 From the State Intellectual Property Office of the People's Republic of China Re. Application No. 201580037467.6. (9 Pages).
Restriction Official Action dated Jan. 16, 2018 From the US Patent and Trademark Office Re. U.S. Appl. No. 14/915,266. (8 pages).
Supplementary European Search Report and the European Search Opinion dated Dec. 1, 2017 From the European Patent Office Re. Application No. 15776016.6. (10 Pages).
Translation of Notification of Office Action dated Nov. 16, 2017 From the State Intellectual Property Office of the People's Republic of China Re. Application No. 201580037467.6. (2 Pages).
Official Action dated Feb. 1, 2019 From the US Patent and Trademark Office Re. U.S. Appl. No. 15/959,397. (31 pages).
Translation dated Jul. 24, 2018 of Notice of Reasons for Rejection dated Jul. 10, 2018 From the Japan Patent Office Re. Application No. 2016-537600 and Its Summary in English. (9 Pages).
Official Action dated Apr. 5, 2018 From the US Patent and Trademark Office Re. U.S. Appl. No. 14/915,266. (62 pages).
Official Action dated Apr. 6, 2018 From the US Patent and Trademark Office Re. U.S. Appl. No. 15/301,968. (52 pages).
Applicant-Initiated Interview Summary dated Apr. 10, 2019 From the US Patent and Trademark Office Re. U.S. Appl. No. 15/959,397. (3 pages).
Translation dated Jul. 18, 2019 of Notification of Reasons for Refusal dated Jun. 25, 2019 From the Japan Patent Office Re. Application No. 2016-537600. (7 Pages).
Notification of Office Action and Search Report dated Apr. 1, 2019 From the State Intellectual Property Office of the People's Republic of China Re. Application No. 201680002365.5 and Its Summary in English. (9 Pages).
Translation dated Apr. 9, 2019 of Notification of Office Action dated Apr. 1, 2019 From the State intellectual Property Office of the People's Republic of China Re. Application No. 201680002365.5. (5 Pages).
Supplementary European Search Report and the European Search Opinion dated Mar. 21, 2019 From the European Patent Office Re. Application No. 16799477.1. (10 Pages).
Decision to Grant Patent dated Jul. 16, 2019 From the Japan Patent Office Re. Application No. 2017-227752 and Its Translation Into English. (6 Pages).
Official Action dated Jul. 31, 2019 From the US Patent and Trademark Office Re. U.S. Appl. No. 15/959,397. (25 pages).

(56) References Cited

OTHER PUBLICATIONS

Notice of Reasons for Rejection dated Jun. 25, 2019 From the Japan Patent Office Re. Application No. 2016-537600 and Its Summary in English. (8 Pages).
Communication Pursuant to Article 94(3) EPC dated May 8, 2020 From the European Patent Office Re. Application No. 14816424.7. (4 Pages).
Notification of Office Action and Search Report dated Jun. 3, 2020 From the State Intellectual Property Office of the People's Republic of China Re. Application No. 201680002365.5 and Its Summary in English. (7 Pages).
Notification of Reason for Refusal dated May 19, 2020 From the Japan Patent Office Re. Application No. 2016-537600 and Its Translation Into English. (10 Pages).
Translation dated Jun. 9, 2020 of Notification of Office Action dated Jun. 3, 2020 From the State Intellectual Property Office of the People's Republic of China Re. Application No. 201680002365.5. (2 Pages).
Notification of Office Action and Search Report dated Apr. 16, 2020 From the State Intellectual Property Office of the People's Republic of China Re. Application No. 201810576718.3 and Its Translation of Office Action Into English. (14 Pages).
Communication Pursuant to Article 94(3) EPC dated Jun. 5, 2020 From the European Patent Office Re. Application No. 17196947.0. (5 Pages).
Notice of Reasons for Rejection dated Jun. 16, 2020 From the Japan Patent Office Re. Application No. 2017-559659 and Its Translation Into English. (9 Pages).
Official Action dated Jul. 1, 2020 from the US Patent and Trademark Office Re. U.S. Appl. No. 15/959,397. (37 pages).
Communication Pursuant to Article 94(3) EPC dated Nov. 11, 2019 From the European Patent Office Re. Application No. 14771962.9. (5 Pages).
Notification of Office Action dated Dec. 16, 2019 From the State Intellectual Property Office of the People's Republic of China Re. Application No. 201680002365.5. (4 Pages).
Translation dated Dec. 30, 2019 of Notification of Office Action dated Dec. 16, 2019 From the State Intellectual Property Office of the People's Republic of China Re. Application No. 201680002365.5. (2 Pages).
Decision to Grant dated Jan. 6, 2020 From the Japan Patent Office Re. Application No. 2016-559518. (3 Pages).
International Search Report and the Written Opinion dated Dec. 26, 2019 From the International Searching Authority Re. Application No. PCT/IL2019/050919. (12 Pages).

\* cited by examiner

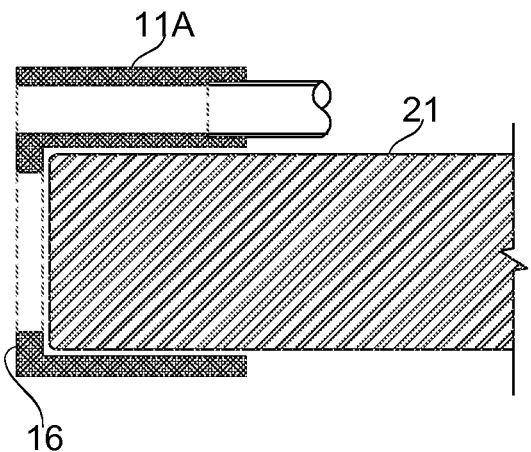
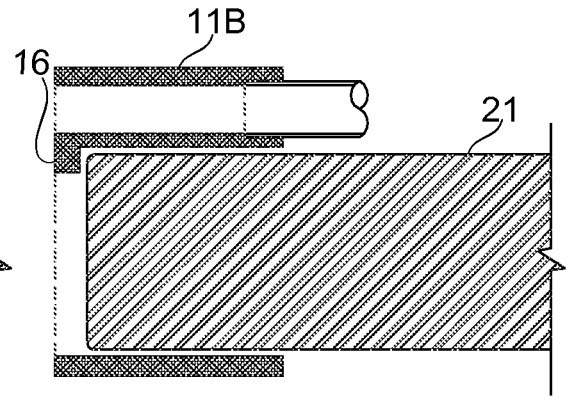
FIG. 11A
FIG. 11B
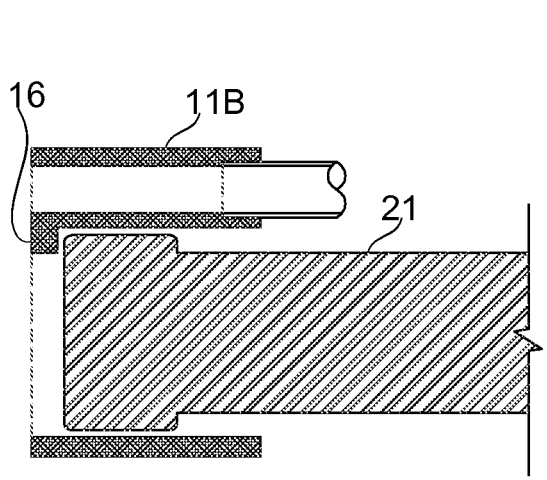
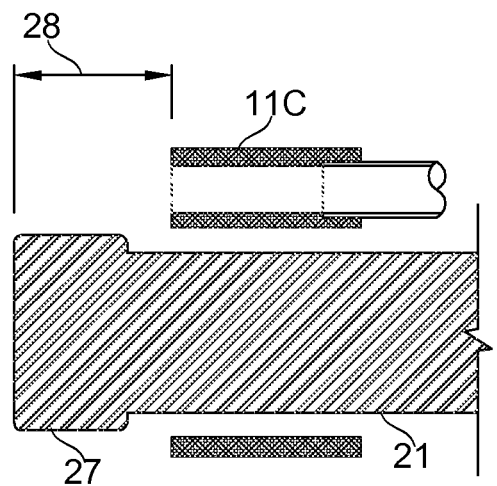
FIG. 11C
FIG. 11D

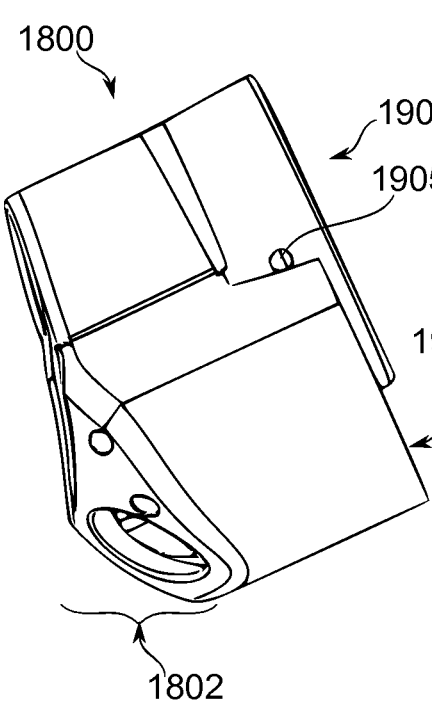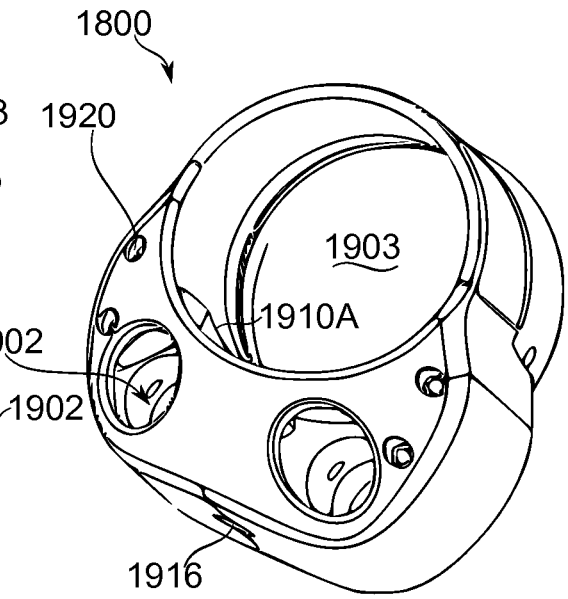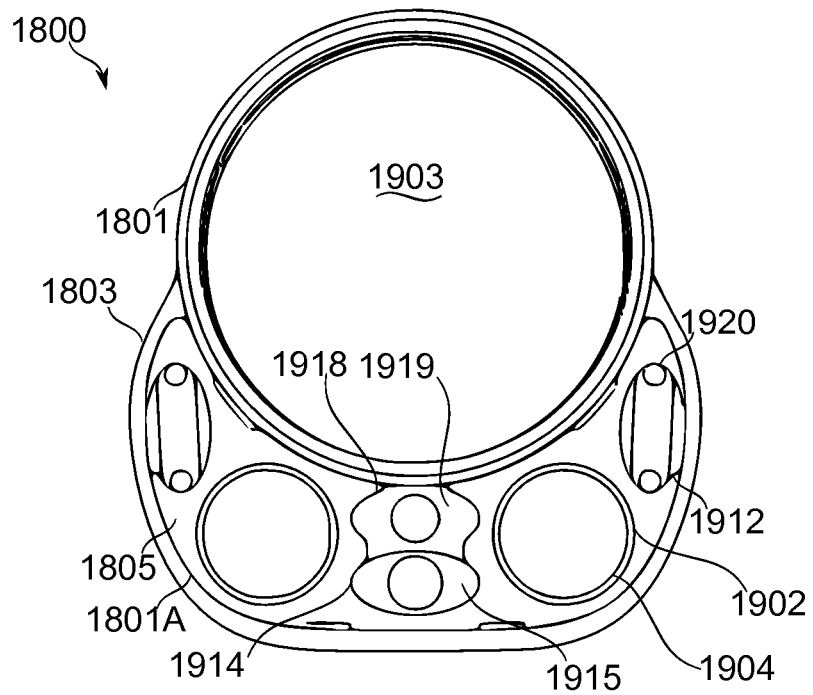

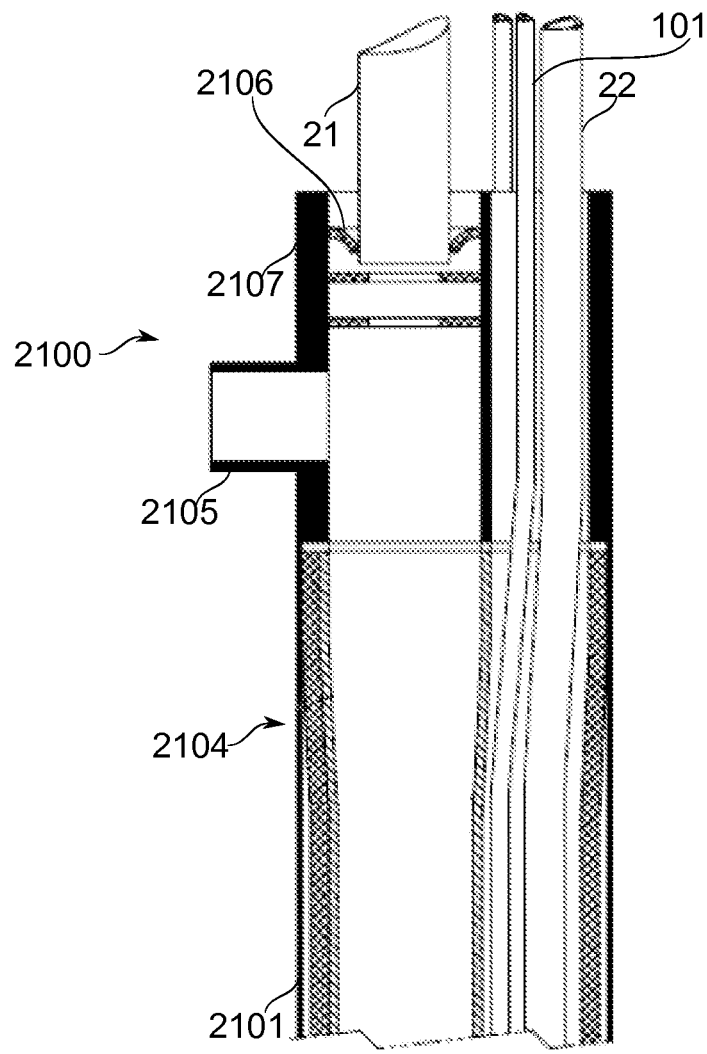
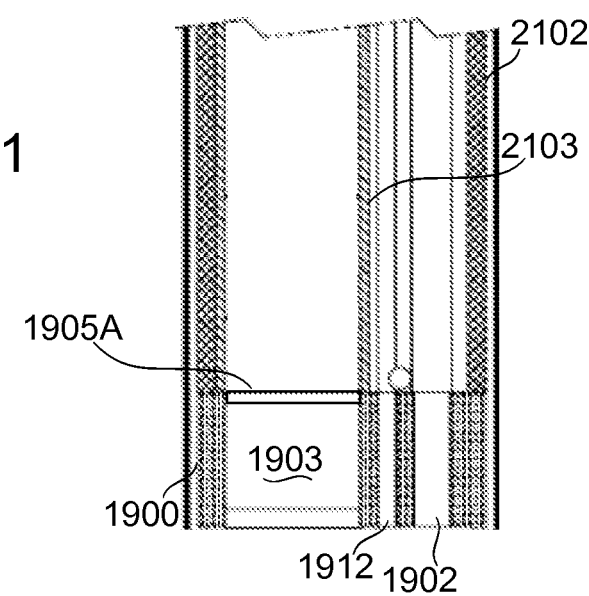
FIG. 21

DISTAL FRONT END FOR COORDINATED POSITIONING OF AN ENDOSCOPE WITH A SUCTION DEVICE

RELATED APPLICATIONS

This application is a Continuation-in-Part (CIP) of PCT Patent Application No. PCT/IL2014/051014 filed on Nov. 20, 2014, which claims the benefit of priority under 35 USC § 119(e) of U.S. Provisional Patent Application Nos. 62/012,997 filed on Jun. 17, 2014 and 61/906,982 filed on Nov. 21, 2013. The contents of the above applications are all incorporated by reference as if fully set forth herein in their entirety.

FIELD AND BACKGROUND OF THE INVENTION

The present invention, in some embodiments thereof, relates to a tool for use with an endoscope and, more particularly, but not exclusively, to components to be inserted in a body lumen together with an endoscope and used to clean the body lumen to facilitate visualization of the lumen by means of the endoscope. For example, some embodiments may be used with a colonoscope for cleaning of a colon during colonoscopy.

During a colonoscopy, fecal matter is removed from a colon using pipes dedicated for the tasks of irrigation and evacuation. Typically, a colonoscope irrigation channel delivers fluid for loosening, dissolving, and/or fragmenting fecal material to the colon; and a working channel evacuates this material.

Self-cleaning systems have been described which add irrigation and/or evacuation channels on to a colonoscope probe; for example, in International Patent Publication Nos. WO 2009/143201, filed May 20, 2009 and WO 2010/138521, filed Dec. 2, 2010.

SUMMARY OF THE INVENTION

According to an aspect of some embodiments of the invention, there is provided a tip adaptor of a colon cleaning system for use with a colonoscope probe comprising a shell having a hollow region sized to fittingly accommodate an insert, the insert comprising a plurality of sockets, each fittingly accommodating the distal end of one or more respective fluid transport tubes, wherein one of the insert and the shell comprises elastically deformable material, and the other comprises a relatively rigid material.

According to some embodiments of the invention, the shell is comprised of a softer material than the insert, and the shell is deformable around the insert in response to external force, while the insert remains in place and substantially undeformed.

According to some embodiments of the invention, the soft shell defines at least one elastically collapsible hollow.

According to some embodiments of the invention, the collapsible hollow comprises a guard wall which extends across and is spaced from an aperture of at least one of the sockets along a longitudinal axis of the socket.

According to some embodiments of the invention, the guard wall comprises an aperture of the collapsible hollow.

According to some embodiments of the invention, the aperture of the socket is a suction intake aperture.

According to some embodiments of the invention, the aperture of the guard wall has substantially the same size and shape as the suction intake aperture.

According to some embodiments of the invention, the guard wall is spaced from the aperture along a longitudinal axis of the socket by at least 5 mm.

According to some embodiments of the invention, the collapsible hollow is sufficiently flexible to elastically collapse upon being pressed from within against a portion of colon wall, the collapse occurring at a force below one that damages the portion of colon wall.

According to some embodiments of the invention, the shell comprises an aperture surrounding an aperture of at least one of the sockets.

According to some embodiments of the invention, the aperture of the socket is an irrigation aperture.

According to some embodiments of the invention, the irrigation aperture is shaped to form fluid into a jet upon the supply of fluid therethrough, and the aperture of the shell is sufficiently large to avoid interference with the jet.

According to some embodiments of the invention, the shell is comprised of a harder material than the insert, and the insert is deformable between the sockets.

According to some embodiments of the invention, the soft insert is sufficiently flexible to deform upon movement of the fluid transport tubes while maintaining fitting contact with the fluid transport tubes and with the hollow region.

According to some embodiments of the invention, the shape of the harder shell is maintained during the deforming.

According to some embodiments of the invention, the tip adaptor comprises a socket sized to receive a distal portion of the colonoscope probe.

According to some embodiments of the invention, the tip adaptor is attached to the distal end of an evacuation channel sized for insertion to a distal segment of a colon.

According to some embodiments of the invention, the adaptor is attached so that it is positioned for suctioning waste to the evacuation channel from the distal segment of a colon when inserted therein.

According to some embodiments of the invention, the tip adaptor comprises a colon spacer integrally formed with the shell, attached to a circumference of the tip adaptor and extending radially therefrom; the colon spacer being sufficiently flexible that it collapses upon receiving pressure due to forward motion of the tip adaptor into a radially restricted region of colon.

According to an aspect of some embodiments of the invention, there is provided a method of navigating a tip adaptor at a distal end of a colon cleaning device, comprising: advancing the tip adaptor to press against a portion of soft tissue; and collapsing a portion of the tip adaptor against the soft tissue, thereby reducing a maximum pressure of the tip adaptor against the soft tissue.

According to some embodiments of the invention, the tip adaptor comprises a plurality of sockets attached to a corresponding plurality of lumens of the colon cleaning device; and the sockets remain undeformed while the portion of the tip adaptor is collapsed.

According to an aspect of some embodiments of the present invention, there is provided a cleaning system for evacuating waste from a tubular digestive tract lumen, comprising: at least one evacuation lumen having a distal end configured for insertion to a distal segment of the digestive tract lumen; the at least one evacuation lumen being configured to transmit suction to the distal end; a guard wall defining a suction inlet at the distal end which is directed away from the nearest tissue of the digestive tract lumen when inserted therein.

According to some embodiments of the invention, the guard wall extends distally from an intake cross-section of the evacuation lumen which comprises the distal-most region having substantially the same cross-section as the main proximal region of the evacuation lumen.

According to some embodiments of the invention, a portion of the distal extension of the guard wall extends medially relative to a central axis perpendicular to the intake cross-section.

According to some embodiments of the invention, the area of the suction inlet defined by the guard wall is larger than the area of the intake cross-section by a factor of at least 2.

According to some embodiments of the invention, the guard wall extends circumferentially around at least a portion of a cross-section of the distal portion of the colonoscope probe when the adaptor is attached to the distal portion.

According to some embodiments of the invention, the guard wall extends entirely around the cross-section.

According to an aspect of some embodiments of the present invention, including, for example, any of the embodiments described herein, there is provided a cleaning system for evacuating waste from a tubular digestive tract lumen, comprising: at least one evacuation lumen having a distal intake aperture configured for insertion to a distal segment of the digestive tract lumen; the at least one evacuation lumen being configured to transmit suction to the intake aperture; a guard wall separating the intake aperture from the nearest tissue of the digestive tract lumen when inserted therein; the guard wall defining a suction inlet positioned to divert the suction away from the nearest tissue.

According to some embodiments of the invention, including, for example, any of the embodiments described herein, the guard wall extends distally from the intake aperture.

According to some embodiments of the invention, including, for example, any of the embodiments described herein, a portion of the distal extension of the guard wall extends medially relative to a central axis perpendicular to the intake aperture.

According to some embodiments of the invention, including, for example, any of the embodiments described herein, a portion of the guard wall continues beyond the central axis from the medially extending portion.

According to some embodiments of the invention, including, for example, any of the embodiments described herein, the area of the suction inlet defined by the guard wall is larger than the area of the intake aperture by a factor of at least 2.

According to some embodiments of the invention, including, for example, any of the embodiments described herein, the extending distally is by at least 5 mm.

According to some embodiments of the invention, including, for example, any of the embodiments described herein, the system comprises an adaptor attachable to a distal portion of a colonoscope probe, wherein the adaptor comprises the guard wall.

According to some embodiments of the invention, including, for example, any of the embodiments described herein, the guard wall extends from a portion of the intake aperture circumferentially around at least a portion of a cross-section of the distal portion of the colonoscope probe, when the adaptor is attached to the distal portion.

According to some embodiments of the invention, including, for example, any of the embodiments described herein, the guard wall extends entirely around the cross-section.

According to some embodiments of the invention, including, for example, any of the embodiments described herein, the guard wall tapers in a distal direction.

According to some embodiments of the invention, the taper ends distally in a blunt surface.

According to some embodiments of the invention, including, for example, any of the embodiments described herein, the guard wall comprises a tapering portion which, when the adaptor and the colonoscope probe are attached, extends into a region defined by perpendicular projection of the distal perimeter of the distal portion of the colonoscope probe distally therefrom.

According to some embodiments of the invention, including, for example, any of the embodiments described herein, the tapering portion extends into the projection-defined region around the whole circumference thereof.

According to some embodiments of the invention, including, for example, any of the embodiments described herein, the diverting comprises angling of the suction inlet at least 30 degrees away from a direction parallel or perpendicular to a distal-proximal axis of a distal portion of the evacuation lumen.

According to some embodiments of the invention, including, for example, any of the embodiments described herein, the distal extending is around at least 20% of a circumference enclosing the intake aperture, extends distally from the intake aperture by at least 5 mm, and comprises a wall at least 0.1 mm thick.

According to some embodiments of the invention, including, for example, any of the embodiments described herein, the guard wall extends distally to a limit defined by exclusion from a field of view of an imaging means comprised in the colonoscope probe.

According to some embodiments of the invention, including, for example, any of the embodiments described herein, the guard wall comprises at least one vent aperture positioned to allow fluid to pass therethrough to a side facing the intake aperture while receiving the suction.

According to some embodiments of the invention, including, for example, any of the embodiments described herein, the at least one vent aperture comprises an open area less than 50% of the area of the suction inlet.

According to some embodiments of the invention, including, for example, any of the embodiments described herein, the pressure differential across the at least one vent aperture is less than half of the maximal pressure differential associated with the suction.

According to some embodiments of the invention, the at least one vent aperture is axially aligned with the suction inlet, and spaced from it by a chamber having an axially transverse section at least as large as the suction inlet.

According to some embodiments of the invention, the chamber further comprises a pressure relief aperture which is in fluid communication with the digestive tract lumen through at least one additional lumenal extent, the pressure relief aperture being positioned along a wall of the chamber extending between the at least one vent aperture and the suction inlet.

According to some embodiments of the invention, including, for example, any of the embodiments described herein, the suction inlet comprises a mouth which is non-planar around the lip thereof.

According to some embodiments of the invention, including, for example, any of the embodiments described herein, the suction inlet comprises a plurality of apertures, the apertures being positioned to be unoccludable simultaneously by a wall region extending around less than a quarter of a circumference comprising portions of the aperture.

According to some embodiments of the invention, including, for example, any of the embodiments described herein, the guard wall separates the intake aperture of at least a second evacuation lumen from the nearest tissue.

According to some embodiments of the invention, including, for example, any of the embodiments described herein, the digestive tract lumen is a colon.

According to some embodiments of the invention, including, for example, any of the embodiments described herein, the suction inlet is large enough to prevent full occlusion by a protruding section of wall which is less than 5 mm in height.

According to some embodiments of the invention, including, for example, any of the embodiments described herein, the suction inlet is protected from at least one side such that it cannot be fully occluded by a continuous section of wall which extends for more than 10 mm beyond the region of contact.

According to an aspect of some embodiments of the present invention, including, for example, any of the embodiments described herein, there is provided a cleaning system for use with a colonoscope probe comprising: an adaptor attached to the distal end of an evacuation channel sized for insertion to a distal segment of a colon; the adaptor being attachable over a distal portion of the colonoscope probe; the distal portion being proximal to a portion of the colonoscope probe having an outer diameter larger than the inner diameter of the adaptor when attached.

According to some embodiments of the invention, including, for example, any of the embodiments described herein, the adaptor is attached so that it is positioned for suctioning waste to the evacuation channel from the distal segment of a colon when inserted therein.

According to an aspect of some embodiments of the present invention, including, for example, any of the embodiments described herein, there is provided a cleaning to system for use with a colonoscope probe comprising: an adaptor attached to the distal end of an evacuation lumen configured for insertion to a distal segment of a colon; the adaptor comprising a gap; the gap being passable over the side wall of a distal portion of the colonoscope probe, and from a direction perpendicular to the side wall, for attachment of the adaptor thereto.

According to some embodiments of the invention, including, for example, any of the embodiments described herein, the adaptor is attached to the distal end of an irrigation channel.

According to some embodiments of the invention, including, for example, any of the embodiments described herein, the gap is widenable to pass over the widest extent of the side wall, the widened gap being narrowable again behind the widest extent to form the attachment.

According to some embodiments of the invention, including, for example, any of the embodiments described herein, the gap is widenable by pulling apart sections of the adaptor on either side of the gap.

According to some embodiments of the invention, including, for example, any of the embodiments described herein, the gap being widenable and narrowable comprises the adaptor being elastically deformable.

According to some embodiments of the invention, including, for example, any of the embodiments described herein, the adaptor comprising a gap is dimensioned for surrounding more than 180 degrees of the circumference of the side wall.

According to some embodiments of the invention, including, for example, any of the embodiments described herein, the adaptor comprising a gap is dimensioned for surrounding more than 270 degrees of the circumference of the side wall.

According to an aspect of some embodiments of the present invention, there is provided a tip adaptor of a colon cleaning system for use with a colonoscope probe comprising: an evacuation inlet region on a distal surface of the tip adaptor, and offset from the radial center of the surface, the evacuation inlet region comprising an aperture configured for connection to a suction source, the suction source being operable while the tip adaptor is inserted to the distal end of a colon while attached to the colonoscope probe; a colon spacer attached to a circumference of the tip adaptor on a side toward which the evacuation inlet region is offset, and extending radially therefrom; the colon spacer being sufficiently flexible that it collapses upon receiving pressure due to forward motion of the tip adaptor into a radially restricted region of colon.

According to some embodiments of the invention, the colon spacer is directed to one side of the tip adaptor.

According to some embodiments of the invention, the collapse comprises bending proximally and substantially parallel to a body of the tip adaptor during passage through the restriction.

According to an aspect of some embodiments of the present invention, there is provided a method of navigating a colon cleaning device through a colon comprising: orienting a colon spacer extending radially from a distal tip adaptor of a colon cleaning system to push the tip adaptor away from a wall portion of the colon, while evacuation suction through the colon cleaning device is applied; and collapsing the colon spacer so that the tip adaptor approaches the wall portion.

According to some embodiments of the invention, the collapsing comprises translating the tip adaptor along a proximal-distal axis while a portion of the colon spacer drags on the colon, such that the flexible member collapses and the tip adaptor approaches the colon wall portion.

According to some embodiments of the invention, the method comprises re-extending the collapsed colon spacer by translating the tip adaptor again.

According to an aspect of some embodiments of the present invention, there is provided a tip adaptor of a colon cleaning system for use with a colonoscope probe comprising a hard shell having a hollow region sized to fittingly accommodate a soft insert; the soft insert comprising a plurality of deformable sockets, each fittingly accommodating the distal end of one or more respective fluid transport tubes.

According to some embodiments of the invention, the soft insert is sufficiently flexible to deform upon movement of the fluid transport tubes while maintaining fitting contact with the fluid transport tubes and with the hollow region.

According to some embodiments of the invention, the shape of the hard shell is maintained during the deforming.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 11A-11C schematically illustrate configurations for cleaning system tip adaptors mountable on distal portions of endoscopes, according to some exemplary embodiments of the invention;

FIG. 11D shows an over-the-end applied tip adaptor, associated with an endoscope distal portion, according to some exemplary embodiments of the invention;

FIGS. 18A-18C schematically illustrate a tip adaptor comprising a shell and insert of different hardness, according to some exemplary embodiments of the invention;

FIG. 21 schematically illustrates a sleeve assembly in a sleeve placement jig together with components of an irrigation system and a colonoscope, according to some exemplary embodiments of the invention;

DESCRIPTION OF SPECIFIC EMBODIMENTS OF THE INVENTION

Figure 1A:
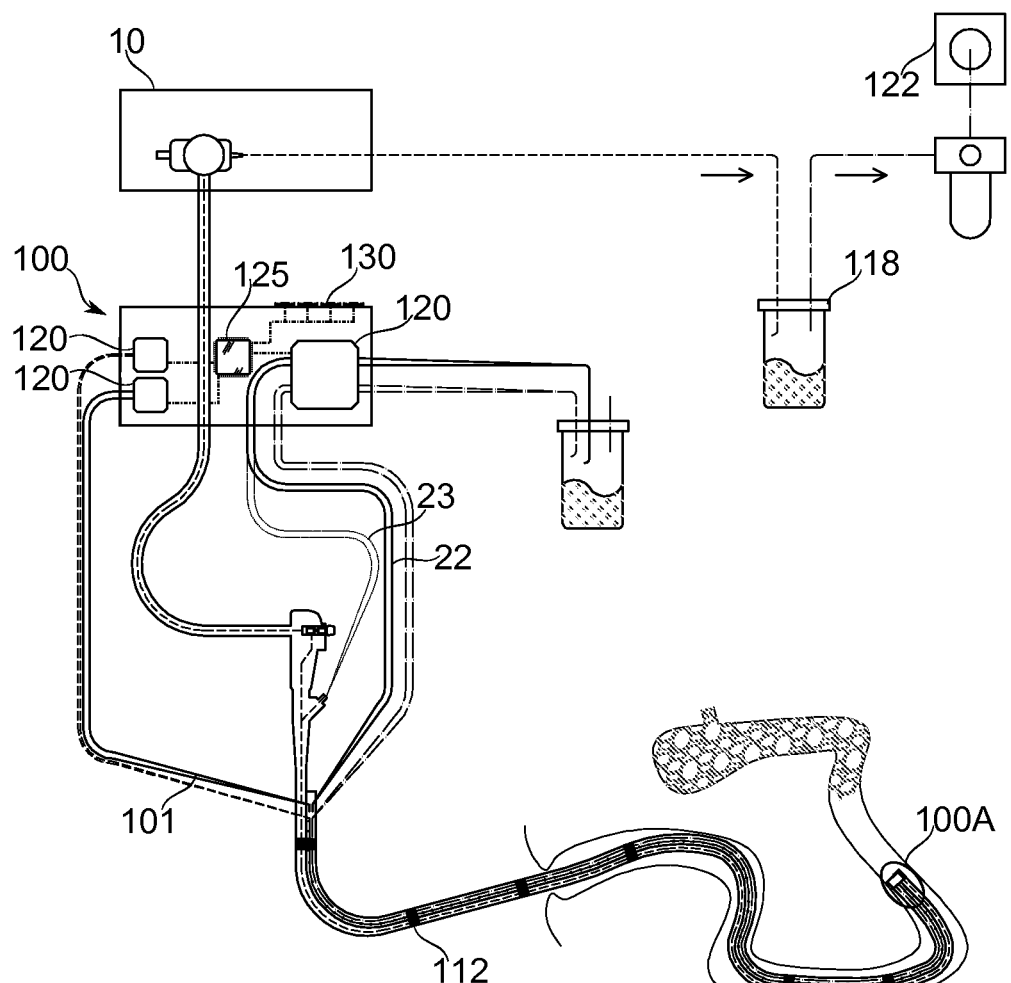
FIGS. 1A-1B present simplified schematic views of a cleaning system usable with an endoscope, according to some exemplary embodiments of the present invention.

The present invention, in some embodiments thereof, relates to a tool for use with an endoscope and, more particularly, but not exclusively, to components to be inserted in a body lumen together with an endoscope and used to clean the body lumen to facilitate visualization of the lumen by means of the endoscope. For example, some embodiments may be used with a colonoscope for cleaning of a colon during colonoscopy.

OVERVIEW

A broad aspect of some embodiments of the invention relates to a tip adaptor for connecting a distal portion of an endoscope with a distal portion of a cleaning module for cleaning of a colon or other body lumen.

In some embodiments of the invention, a probe of the lumen-cleaning module (cleaning system) is dimensioned for reaching to the end of a colon, or to another portion of a gastrointestinal tract. In some embodiments, the lumen-cleaning module is adapted for pumping irrigation fluid to the distal end of the probe to dislodge, disaggregate, dissolve, and/or suspend fecal matter in a colon. In some embodiments, the lumen-cleaning module is adapted for evacuating loosened fecal matter from the colon through a lumen of the probe.

An aspect of some embodiments of the invention relates to a two-hardness or multiple-hardness construction of a tip adaptor, for example, such that an outer portion of the tip adaptor is relatively rigid, and an insert to said outer portion is relatively soft, and/or, for example, such that an outer portion of the tip adaptor is relatively soft, and an insert to said outer portion is relatively hard.

In some embodiments of the invention, a soft insert and hard outer portion are provided.

In some embodiments of the invention, the soft insert comprises sockets sized to receive connections to fluid transport tubes such as evacuation channels, irrigation fluid supply conduits, and/or pressure sensing tubes. In some embodiments, the soft insert serves to absorb and/or buffer movements of the fluid transport tubes, such that displacements due to tube motion relative to the tip are distributed in the body of the soft insert, rather than focused to the interface region between the fluid transport tubes and their respective sockets. In some embodiments, the hard portion of the tip adaptor is sufficiently hard to resist deformations due to direct external forces likely to be encountered during navigation of a colon. Potentially, this helps to shield the socket connections from deformations that might tend to loosen connections. Potentially, the relatively inflexible construction of the hard portion of the tip adaptor resists deformations that might tend to allow the tip to become impacted upon rather than slide over protrusions in the intestinal wall.

In some embodiments, the deformability characteristics of the soft insert comprise movement of about 0.1 mm in response to between 1-10 Newtons of force. In some embodiments, movement corresponds to about 0.1-0.25 mm, 0.15-0.2 mm, 0.25-0.5 mm, or range of movements having the same, greater, smaller, and/or intermediate bounds.

In some embodiments of the invention, a hard insert and soft outer portion are provided.

Optionally, the hard insert comprises sockets sized to receive connections to fluid transport tubes such as evacuation channels, irrigation fluid supply conduits, and/or pressure sensing tubes. Optionally, use of a relatively hard insert to a soft outer portion allows manufacturing of sockets to tight tolerances for receiving fluid transport and/or pressure sensing tubes, while still allowing a soft outer portion which mitigates potentially traumatic interactions between the device head and surrounding tissue during operation.

Potentially, use of a relatively hard insert provides dimensional stability during storage and/or in use. For example, stability of the connection of the socket to tubing is preserved by the hard insert being substantially resistant to deformation under the forces of use, and/or due to forces or creep during storage. Optionally a relatively hard insert provides dimensional stability of an aperture, for example, an aperture shaped to form and/or direct a fluid jet for cleaning. Without dimensional stability of a jetting aperture, jet force, shape, and/or direction is potentially altered during storage and/or use.

In some embodiments, a soft outer shell of the tip adaptor reduces the potential for trauma in the tissue due to interactions with the tip adaptor. For example, the surface of the tip adaptor itself has some rubbery give to it, allowing distribution of forces to potentially prevent focusing force to a small region of soft tissue. In some embodiments, one or more portions of the tip adaptor soft shell are configured to partially and elastically collapse when receiving force, providing still further give in the tip adaptor shape.

In some embodiments, apertures (such as jet and/or suction apertures) which are defined and made dimensionally stable by a hard insert portion are protected by a surrounding portion of soft shell. For example, the soft shell is provided with an aperture wide enough to avoid interference with the function (for example, shape and/or aiming) of a jet aperture, and surrounding the jet aperture to prevent direct tissue interactions with it. Optionally, a soft shell aperture is provided spaced from and in front of a hard insert-defined suction aperture, potentially protecting tissue from encountering a hard edge of the suction aperture.

In some embodiments, the deformability characteristics of the soft shell (for example, the shell where it directly overlies a hard insert portion) comprise movement of about 0.1 mm in response to between 1-10 Newtons of force. In some embodiments, movement corresponds to about 0.1-0.25 mm, 0.15-0.2 mm, 0.25-0.5 mm, or a range of movements having the same, greater, smaller, and/or intermediate bounds. In some embodiments, the soft shell comprises one or more collapsible chambers and/or hollows, and is configured to allow elastic collapse to an extent (for example, of 1 mm, 2 mm, 3 mm, 4 mm, 5 mm, or another greater or smaller extent) which is at least partially determined by the dimensions of the chamber or hollow, for example in response to between 1-10 Newtons of force. The hollow is likewise, for example, about 1 mm, 2 mm, 3 mm, 4 mm, 5 mm, or another greater or smaller distance in extent in the direction of collapse. Alternatively—for example, in embodiments where the chambers are sealed—the collapse is to an intermediate range governed by the compressibility of the chamber walls and/or contents.

It is to be understood that the extent and/or contiguity of the relatively hard and relatively soft parts of the tip adaptor is optionally subject to further variations and combinations. Optionally, for example, a shell comprises both hard and soft portions. For example, corners, leading surfaces, and/or other surface of the shell are formed as soft, yielding, and/or compressible portions of the shell, while other parts of the shell (exposed as surfaces and/or supporting the compressible portions from within) are formed as relatively hard portions of the shell. Additionally or alternatively, the insert portion is formed with hard, stiff, and/or incompressible portions which provide dimensional stability of parts such as socket shapes and irrigation inlet shapes, together with, for example, soft linings of sockets (potentially to allow slight deformation upon experiencing force, but thin enough so that the functionally important dimensional stability provided by the hard portion is not compromised). Additionally or alternatively, a hard socket and/or irrigation inlet is embedded within a matrix of softer material. Potentially, this allows some give and/or relative motion of sockets to absorb forces exerted on the tip, while preserving dimensional stability needed, for example, to securely hold fittings and/or reliably shape jet formation Thus, a tip adaptor is optionally provided with multiple layers of alternating hardness and softness, within the shell and/or within the insert, which potentially allows providing at least some of the advantages of each material type.

Furthermore, although the embodiments herein are described with respect to an optionally separable "shell" and "insert", it is to be understood that both elements are optionally manufactured as a single unit. Alternatively, either element is optionally manufactured as a plurality of parts, which optionally interconnect to one another, and/or are held to the tip adaptor by the complementary part or assembly of parts. For example, in some embodiments, an insert is optionally formed as a plurality of inserts which are separately fit into the shell. Additionally or alternatively, a shell is formed of parts which attach separately to an insert, for example, by being molded into place, by a snap fit, and/or by adhesive attachment.

Moreover, it is to be understood that the terms "soft" and "hard" as used herein relate to the relative elastic deformability of materials and/or construction (including plastic polymer compositions such as polyurethane, and/or constructions comprising hollows, thin walls, or other deformable and/or reducible shapes), and, in particular, deformability in response to compressive forces.

An aspect of some embodiments of the invention relates to structures for protecting colon tissues from accidental damage by suction used for evacuation of fecal material.

In some embodiments of the invention, an intake guard is provided as a portion of a tip adaptor. In some embodiments, the intake guard comprises a wall positioned to divert suction into the intake of an evacuation channel away from the tissue of a lumenal wall during insertion to a colon. It is a potential advantage to provide such a guard wall, as the intake aperture of the evacuation port is subject in some embodiments to suction.

Tissue approaching an unshielded evacuation port may be damaged by suction, particularly if the tissue seals across the port such that the pressure gradient drop occurs substantially across the tissue. Another potential advantage of a guard wall is to protect the function of evacuation port itself. In some embodiments, a sensor system allows a controller to reduce and/or reverse suction strength upon detection of an occlusion of the system. It is a potential advantage to reduce the occurrence of occlusions by tissue in order to maintain a higher rate of evacuation throughput by the cleaning system.

The "intake aperture" or "intake cross-section" of the evacuation lumen refers to the most distal region of the evacuation lumen where the evacuation lumen is substantially uniform in cross-section (for example, within ±10% of its diameter and/or cross-sectional area along the main body of the evacuation lumen). In embodiments where a guard wall forms the last portion of the evacuation lumen, the intake aperture or intake cross-section terminates where the guard wall shape defines (or, where change is continues, where it begins to define, for example by a slope change) a substantial change in the shape of the evacuation lumen cross-section. A "suction intake" or "suction inlet" marks a region beyond which fluid is not in the evacuation lumen at all. The region interconnecting a suction intake and an intake aperture or cross-section is defined, in some embodiments, by a guard wall. In some embodiments, the interconnecting region comprises an evacuation antechamber.

In some embodiments, the suction intake defined by the guard wall is of a larger diameter than the evacuation lumen or lumens it protects, for example, larger in area by 50%, 100%, 200%, 500%, or another intermediate, smaller, or larger difference. It is a potential advantage for the suction intake to be larger, such that it is more difficult to bring tissue close to it where the tissue experiences a high pressure gradient. In some embodiments of the invention, the suction intake is formed to a non-circular shape, such as an oval, crescent, and/or slit. In some embodiments of the invention, a shortest distance across the suction intake is smaller than the smallest dimension across an evacuation lumen, for example, 75%, 50%, 25%, or an intermediate, larger, or smaller relative size. In some embodiments, the distance of maximum distal extension of the guard wall is, for example, 3-5 mm, 4-10 mm, 6-15 mm, 10-20 mm, or another shorter or longer distance. In some embodiments, the thickness of the intake guard wall is at least 0.1-0.2 mm, 0.1-0.3 mm, 0.2-0.5 mm, 0.4-1.0 mm, or another larger or smaller thickness.

According to the embodiment, the inner diameter of an evacuation channel extended by a guard wall is, for example, 2.1 mm, 3 mm, 4 mm, 4.2 mm, 4.5 mm, 5 mm, 5.5 mm, 6 mm, another larger or smaller diameter, or any diameter in between. The number of evacuation channels which a guard wall protects may be 1, 2, 3, 4 or more evacuation channels, according to the embodiment.

It is a potential advantage for the suction intake to have such a smaller relative dimension, to help ensure than particles which pass it are small enough in at least one dimension to pass through the evacuation lumen without occluding it. It is also a potential advantage for the suction intake to have a dimension of relatively large extent (for example the length of a slit or oval, which may itself be straight and/or curved), such that it is unlikely that any single large particle could act to block it completely. In some embodiments, the ratio of longest to shortest dimension of a suction intake is, for example, 1:2, 1:3, 1:5, 1:10, or another intermediate, smaller, or larger ratio.

In some embodiments of the invention, the intake guard is adapted with one or more additional features which avoid interference with and/or support functioning of the endoscope probe and/or cleaning system. In some embodiments, the intake guard, extending distally from the endoscope probe end, is provided with a tapering shape. The intake guard, in some embodiments, is more fully circumferential (optionally, fully circumferential) than is required simply to shield the evacuation port. It is a potential advantage to provide a taper on the intake guard, for example, so that the narrower tip presented thereby can insert into (and potentially help to pry apart) intestinal constrictions during forward navigation. The wall of the intake guard tapers, for example, to the diameter of the distal end of the colonoscope probe. In some embodiments, the guard tapers more or less, for example, to within about 120% of the colonoscope probe diameter, or within about 100%, 90%, 80%, 50% or another larger or smaller relative taper diameter. In some embodiments, the tapering extent is different at different circumferential locations. For example, a taper, in some embodiments, is shorter (distally) and/or wider (radially) at a portion of the adaptor which is closer to an imaging and/or illumination means comprised within the colonoscope. Potentially, this avoids blocking the view and/or casting a visible shadow. In some embodiments, the taper begins behind the distal end of a colonoscope, and terminates at about the distal end.

In some embodiments, the intake guard is provided with one or more vent apertures that allow fluid to cross the intake guard wall, while still preventing tissue of a lumenal wall from approaching regions of high negative pressure. In some embodiments, apertures are positioned at locations on the guard wall which are sufficiently far from the region of maximal pressure drop that there is no damaging pressure drop across them. This may be, for example, near the open end of the guard wall that defines the suction aperture. Additionally or alternatively, an aperture is located or near an interior cross-section defined by the guard wall which is relatively large, such that flow is slower, and the pressure drop correspondingly less. Potentially, having a dedicated, wall- and/or debris-protected suction aperture separate from the vent apertures reduces the pressure gradient across the vent apertures to a level which is unable to grab and/or injure intestinal tissue.

A vent aperture provides a potential advantage for allowing more complete removal of fluid from a body lumen. A guard wall, for example, might otherwise act as a barrier (for example, because of an inward taper) that prevents fluid from reaching proximity to the evacuation port.

In some embodiments, an intake guard is shaped to a rounded distal surface, for example, a surface approximating the surface of a sphere, ovoid, or other substantially rounded shape having a radius of about 10-20 mm. In some embodiments, the surface curvatures approximate a radius within a range of about 5-15 mm, 10-25 mm, 15-25 mm, 20-30 mm, or another range of radii having the same, larger, smaller and/or intermediate bounds.

In some embodiments, an intake guard positions vent apertures (evacuation channel access apertures) such that an evacuation antechamber is positioned between the vent apertures and the intake apertures of the evacuation chamber itself. In some embodiments, the evacuation antechamber comprises an open region fluidly interconnecting a plurality of evacuation intake apertures proximally. In some embodiments, the evacuation antechamber comprises another aperture which is positioned in a location sheltered from waste and/or intestinal wall suction contact (for example, in fluid communication with a lumen of the tip which is difficult to block, due the size, shape and/or position of its own openings). Potentially, the sheltered aperture acts as a pressure shunt to prevent a suction gradient from increasing across one or a plurality of vent apertures if the one or plurality of vent apertures is blocked (for example, by waste particles).

In some embodiments, vent/access apertures are arranged axially in line with evacuation intake apertures, at a size about equal to or smaller than the intake apertures. Potentially, this relative positioning and relative size allows the access apertures to operate as size- and/or orientation-selective filters for waste particles entering the evacuation antechamber, such that fewer waste particles reach the relatively high suction gradient of the intake aperture that are too large and/or oriented to block it.

An aspect of some embodiments of the invention relates to variable-site positioning for a tip adaptor which mates a cleaning system probe to an endoscope probe.

In some embodiments of the invention, the tip adaptor is mateable to a distal end of an endoscope probe directly from the side. In some embodiments, this is obtained by a slit along the side of the tip adaptor which is expandable to receive the endoscope probe, and contractible to lock the tip around the endoscope probe. Optionally, the expandability and contractibility comprise elasticity of the tip adaptor materials. In some embodiments of the invention, the tip adaptor is mateable to a distal end of an endoscope probe over the distal end of the endoscope probe, and configured to be tightened around a portion of the endoscope probe proximal to the end. Potentially, one or both of these configurations allows a tip adaptor to be positioned for a desired balance between: sufficiently distal to provide colonic cleaning but sufficiently proximal to reduce interference with probe navigation in a lumen.

In some embodiments, an endoscope probe is provided with an expanded tip (for example, to accommodate structures for endoscope functions) and a cleaning system tip adaptor is attachable proximal to this expansion. It is a potential advantage to attach proximal to the region of expansion, since this allows a tip adaptor, in some embodiments, to conform to a smaller-diameter region. Conforming to a smaller-diameter region in turn potentially reduces the overall diameter added to the distal portion of the endoscope probe by the cleaning system probe.

An aspect of some embodiments of the invention relates to a flexible guard wall which acts as a variable-distance standoff between a cleaning system tip adaptor and the intestinal wall.

In some embodiments, the guard wall is positioned to stick radially away from the position of the fluid access and/or intake aperture of an evacuation channel, such that suction applied to the evacuation channel is restricted from pulling intestinal wall portions up to the aperture itself (with potentially resulting injury). In some embodiments, the wall is provided with sufficient stiffness to act as a spring that bends to convert distal-proximal motions of the colon cleaning distal end into motion across the transverse cross-section of the colon. For example, with the guard wall bent backward from the tip adaptor (bent proximally) the tip body moves toward or away from the wall as the tip is advanced distally or proximally, respectively. In some embodiments, this motion is used to aim jets, set a level of tip immersion for evacuation, and/or select a tip position for navigation of a restriction, constriction, and/or barrier to distal movement.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

For convenience of exposition, cleaning systems, modules, and/or methods described herein are sometimes referred to as "colon cleaning" systems, modules and/or methods. Colon cleaning is contemplated as a common use of embodiments of the invention. However, it is to be understood that methods and devices taught herein may also be used to clean other portions of an intestine and/or other body lumens.

Accordingly, the term "colon cleaning" as applied to these methods and devices encompasses cleaning not only the colon, but also other portions of an intestine and/or other body lumens. For example, some embodiments of the invention are potentially useful in cleaning as part of a procedure for diagnosing and treatment bleeding in the upper GI tract.

REFERENCE EMBODIMENT

Figure 1B:
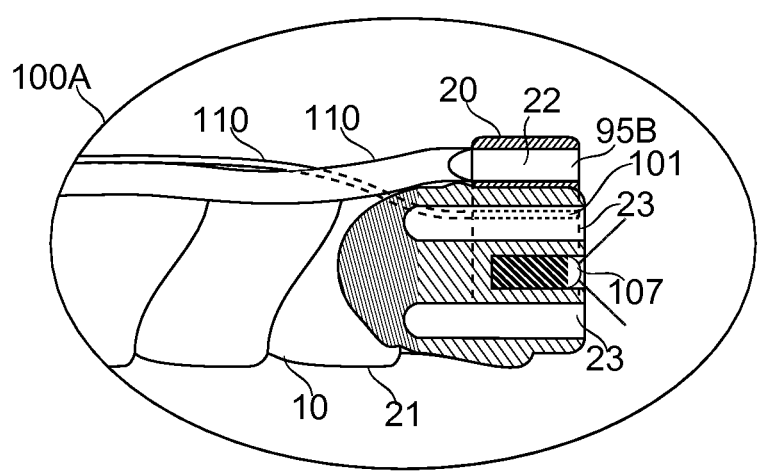

Reference is now made to FIGS. 1A-1B, which are simplified schematic views of a cleaning system 100 usable with an endoscope 10 (which may be a colonoscope), according to some exemplary embodiments of the present invention. FIG. 1B shows inset region 100A of FIG. 1A in greater detail.

In some embodiments cleaning system 100 comprises an endoscope 10, and in some embodiments cleaning system 100 is independent of and optionally usable with an endoscope 10. In some embodiments, system 100 may also be used independently as an insertable cleaning system not connected to or used with an endoscope.

System 100 comprises an interface device 20 which in some embodiments is designed to be disposable, i.e. for one-time use. In some embodiments interface 20 is a distal portion of cleaning system 100, and serves to connect system 100 to a distal portion of an endoscope 10, as shown in the figure. In some embodiments, endoscope 10 is a colonoscope. In some embodiments, endoscope 10 comprises an imaging port 107 and/or other imaging means at a distal portion thereof 21.

Interface 20 is optionally attached to at least one and optionally a plurality of flexible tubes 110, also optionally disposable. In some embodiments flexible tubes 110 are sufficiently long to connect interface 20 to proximal components of cleaning system 100 while interface 20 and a distal portion of endoscope 10 are advanced into a body lumen such as a colon. In an exemplary embodiment tubes 110 are 4 meters long. In other embodiments, tubes 110 are between 2 and 5 meters long. Optionally, tubes 110 are taped or otherwise temporarily attached to endoscope 10 by attachments 112 (e.g. biocompatible tape, or releasable clamps positioned at convenient intervals, for example about every 10-20 cm, every 5-35 cm, or over another longer or shorter interval). Tapes may optionally be localized tape portions, and may optionally be one or more long tape pieces spirally wrapped around an endoscope and its accompanying tubes.

In some embodiments (for example, any of the interface device embodiments described herein), the distal portion of a colonoscope probe 21 has a diameter, of, for example, 5-8 mm, 6-10 mm, 8-12 mm, 10-15 mm, 14-20 mm or another range of diameters having range boundaries equal, higher, lower, or intermediate to the ranges given. A colonoscope distal end diameter may be variable within, for example, the distal 1-10 cm of its length, due to irregularities in construction, structures for steering, and/or structures for containing colonoscope instrumentation. An interface device for connecting to the distal end of a colonoscope probe extends, for example, 1-2 mm, 2-5 mm, 4-8 mm, 6-12 mm, 10-20 mm, 10-30 mm, or another range of distances having bounds equal, intermediate, smaller, or larger.

In some embodiments, tubes 110 are positioned around endoscope 10, may wrap around endoscope 10 and/or around each other, and in general are positioned with respect to endoscope 10 according to convenience and/or in a manner which enhances simplicity of operation and/or flexibility of body-insertable portions of system 100 together with endoscope 10.

In some embodiments, tubes 110 comprise an evacuation channel 22 which connects interface device 20 to a vacuum source, which may for example be a pump 120 and/or a connection to a centralized vacuum system 122 such as are available in some hospitals and clinics. In some embodiments, system 100 comprises a plurality of evacuation channels 22 (also called "suction tubes 22" herein), such as for example two, or three, or four, or more tubes 22. In some embodiments, a lumen of an endoscope working channel 23 is usable as an evacuation channel. In some embodiments, a pump 120 is reversible to purge an evacuation channel. According to the embodiment, the inner diameter of an evacuation channel is, for example, 2.1 mm, 3 mm, 4 mm, 4.2 mm, 4.5 mm, 5 mm, 5.5 mm, 6 mm, another larger or smaller diameter, or any diameter in between.

In some embodiments, interface device 20 (and/or any of the other interface devices described herein) comprises structure which adapts from the intake aperture of an evacuation channel 22 to another shape at the distal-most portion of the suction intake, for example, a slit, an oval, an annulus, and/or a partial annulus. In some embodiments, two or more evacuation channels are combined into a single suction inlet by the interface device. In some embodiments, a single evacuation channel is split into two or more separate suction inlets. In some embodiments, the area of the suction inlet aperture is larger than the cross-section of the evacuation channel lumen, for example, 50% larger, 100%, 150%, 300%, 500%, or another intermediate, larger or smaller difference in area.

In some embodiments one or more or tubes 110 serves as an irrigation tube 101, connected to a fluid source which is a source of water or another liquid and/or a liquid/gas combination. In some embodiments, one or more working channels of endoscope 10 serves as irrigation tube 101.

In some methods of use, irrigation tube 101 supplies a cleaning fluid to interface device 20, which delivers it into a body lumen such as a colon, optionally under pressure, where it serves to wash the colon, and loosens and partially dissolves fecal matter which is then suctioned into one or more suction portals (also called "suction inlets" herein) 95B in interface 20 (as shown in figures discussed below), and thence into evacuation channel 22 and/or 23, which transport the material out of the body and deliver it to an optional fecal matter collector 118. Vacuum (i.e. suction) in tubes is optionally regulated by a valve or regulator or variable pump 120, optionally connected to vacuum source 122. Delivery of suction to tube(s) 22 and of irrigation fluid to tube(s) 101 is optionally regulated by a controller 125, optionally receiving commands from an operator through a user interface 130 such as a computer console and/or a knob or lever or other manual command.

Vacuum Shield

Figure 2A:
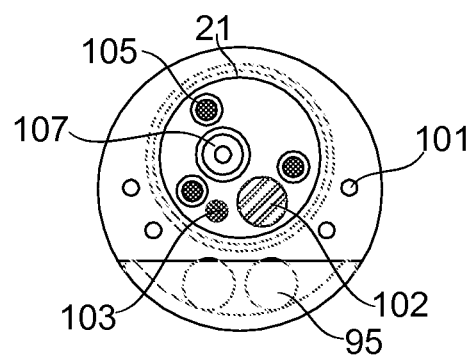
FIGS. 2A-2C schematically illustrate a tip adaptor which comprises a shield, according to some exemplary embodiments of the invention.
Figure 2B:
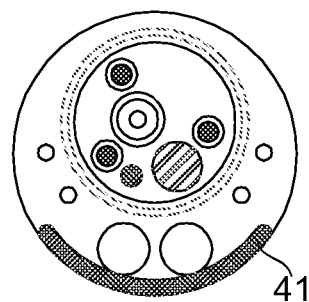
Figure 2C:
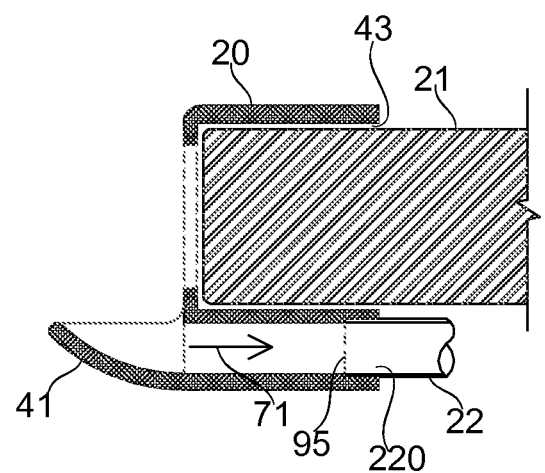

Reference is now made to FIGS. 2A-2C, which schematically illustrate a tip adaptor 20 which comprises the wall of an intake guard 41, according to some exemplary embodiments of the invention.

For some embodiments of the invention, FIGS. 2C and 2A-2B present side cross-sectional and end cross-sectional views at different depths respectively of a tip adaptor 20 comprising an intake guard 41 designed to distance body tissue from an evacuation portal 95 which might be blocked by body tissue and/or which might damage body tissue.

In some embodiments, intake guard 41 is positioned between an evacuation portal such as portal 95 and tissues of a body when said tip adaptor is inserted in a body lumen. For example, intake guard 41 protects tissues of the walls of a colon when suction is applied to the colon through evacuation portal 95. In some embodiments, intake guard 41 extends along at least 20% of the circumference of tip adaptor 20, extends distally from tip adaptor 20. In some embodiments, intake guard 41 extends along at least 35%, 50%, 80%, or 100% of the circumference of tip adaptor 20, or a lesser fraction of the circumference, or any intermediate circumference fraction. In some embodiments, the distance of maximum extension of intake guard 41 is, for example, 3-5 mm, 4-10 mm, 6-15 mm, 10-20 mm, or another shorter or longer distance. The distance of shortest extension at any given point around its circumference, in some embodiments, is between 0 mm and any distance up to the longest distance of extension. In some embodiments, the thickness of intake guard wall 41 is at least 0.1-0.2 mm, 0.1-0.3 mm, 0.2-0.5 mm, 0.4-1.0 mm, or another larger or smaller thickness. In some embodiments, intake guard 41 is rigid or semi-rigid, such that it maintains its shape under at least the pressure used to normally advance the endoscope probe into the body lumen. A rigid or semi-rigid intake guard 41 potentially assists in forward penetration of an advancing distal end of an endoscope probe. In some embodiments, intake guard 41 is flexible, sufficiently so that it collapses, for example, when pressed directly to a lumenal wall. This is a potential advantage for reducing injury as an endoscope probe advances. In some embodiments, intake guard 41 is designed with a flexibility/rigidity which comprises both navigation assistance and safety collapse, such that it collapses, for example, under an advancing pressure of 1-4 PSI, 3-8 PSI, 5-10 PSI, 8-15 PSI, or another higher or lower threshold of pressure. Intake Guard 41 is an optional feature of any of the cleaning systems and/or tip adaptors described herein.

Protection offered by intake guard 41 is potentially by one or more of a selection of mechanisms, as now described, and/or by another mechanism. In some embodiments, shield 41 positions a suction inlet which is in fluid communication with an evacuation lumen 22 to a location and/or orientation which is less exposed to wall contacts than the bare intake aperture 95 of the evacuation lumen 22.

Optionally, the position is a more medial position, potentially increasing a distance between a body lumen wall and a region of a high pressure gradient. Optionally, the orientation is shifted to make contacts with the wall less likely, for example, a rotation which is about mid-way between an orientation perpendicular to the distal-proximal axis of the device (which may tend to come into contact with wall protrusions during distal motion) and an orientation parallel to the distal-proximal axis (which may tend to come into contact with flat regions of the wall). Mid-way, in some embodiments of the invention, comprises an angle which is at least 30° degrees away from both axes, or at least 35°, 40°, or another intermediate, larger, or smaller angle of separation. In some embodiments, the aperture is both moved and rotated. For example, the suction inlet illustrated in FIGS. 2A-2C, defined by the protruding wall section of intake guard 41, rotates the suction inlet by about 90° to point in a medial direction, and moves the aperture in a medial direction.

In some embodiments of the invention, intake guard 41 protects by adopting a shape which is unlikely to be matched by an occluding section of wall. For example, the lip of the intake guard may be formed to define non-planar aperture mouth (for example, the margin of the intake guard forms a lip which is not substantially contained within a single plane), and/or the aperture mouth may be guarded on one or more sides by structures that prevent a wall section from overlying the aperture. For example, the distal end of the colonoscope itself prevents the aperture of intake guard 41 in FIG. 2C from being fully occluded by a large extent of intestinal wall. In some embodiments, interference in the region of the suction inlet mouth prevents fully occlusion by an extent of wall which is continuous beyond 10 mm from the point of contact, or beyond 5-10 mm, 10-15 mm, 8-20 mm, or another range of continuous extent having bounds which are the same, intermediate, smaller, or larger.

In some embodiments of the invention, intake guard 41 protects by creating a larger suction inlet area, decreasing the likelihood of total occlusion. For example, irregularities 1A of an intestinal wall are limited in size, so a sufficiently large aperture, even if oriented to the surface of the irregularity, is not occluded. In some embodiments of the invention, the suction inlet is large enough to prevent total occlusion by a flap of tissue which is less than 5 mm in protruding extent. In some embodiments, occlusion is prevented for flaps of tissue having protruding extent less than 5-10 mm, 2-5 mm, 8-12 mm, or another range of extents having bounds equal, intermediate, larger, or smaller.

Another potential advantage of a large suction inlet area is to help ensure that regions of high pressure differential with the intracolonic pressure are located deep within the intake structures of the evacuation channel and/or intake guard, rather than exposed near the intake aperture itself.

Figure 7A:
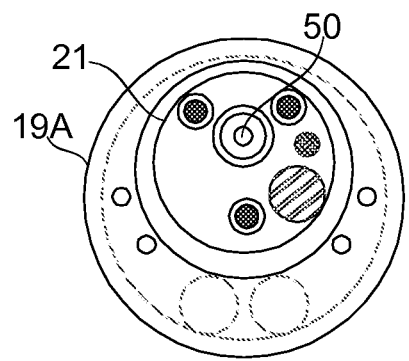
FIGS. 7A-7C schematically illustrate an example of a tip adaptor comprising a fully circumferential shield, according to some exemplary embodiments of the invention.
Figure 7B:
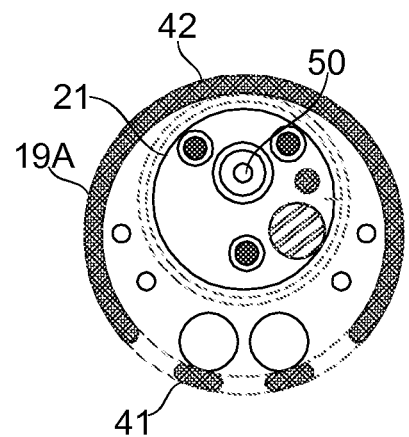
Figure 7C:
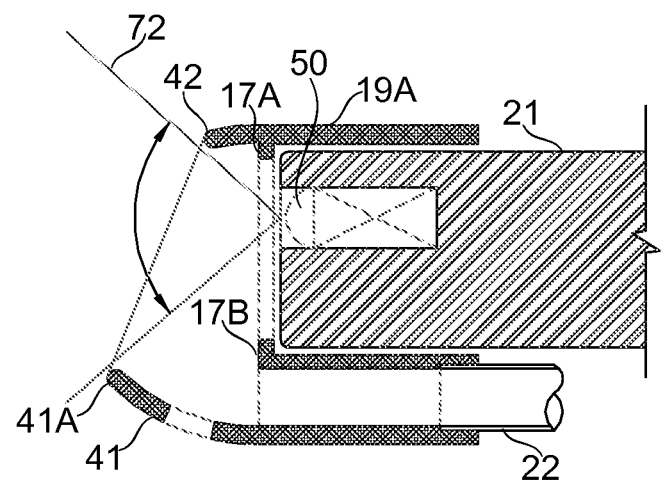

Reference is now made to FIGS. 7A-7C, which schematically illustrate an example of a tip adaptor 19A comprising a fully circumferential intake guard 41, according to some exemplary embodiments of the invention. FIGS. 7A-7B show frontal views at different section planes. FIG. 7C shows a view in horizontal cross-section.

In some embodiments, intake guard portion 42 protrudes a shorter distance away from the tip than a region 41A protecting evacuation lumen 22. A potential advantage of a fully circumferential intake guard 41 is to provide a narrower entry point for an advancing into a body lumen.

In some embodiments, the shorter region 42 is positionable to be radially nearer to an imaging device 50, to reduce or prevent obstruction of a field of view 72 of imaging device 50 by the extension of intake guard 41. In some embodiments, one or more positioning elements 17A, 17B act to ensure proper relative positioning of tip adaptor 19A relative to the end of distal endoscope region 21.

Figure 8A:
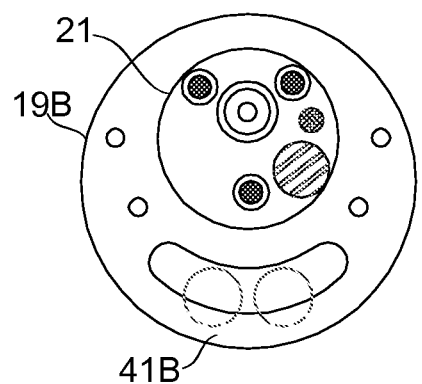
FIGS. 8A-8C schematically illustrate an example of a tip adaptor comprising an end-recessed shield, according to some exemplary embodiments of the invention.
Figure 8B:
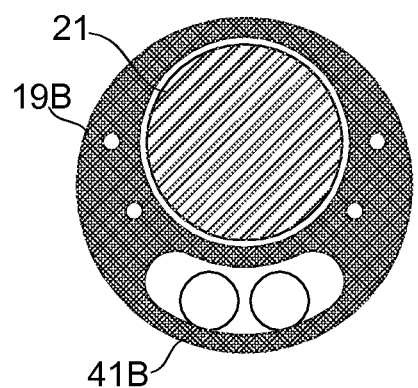
Figure 8C:
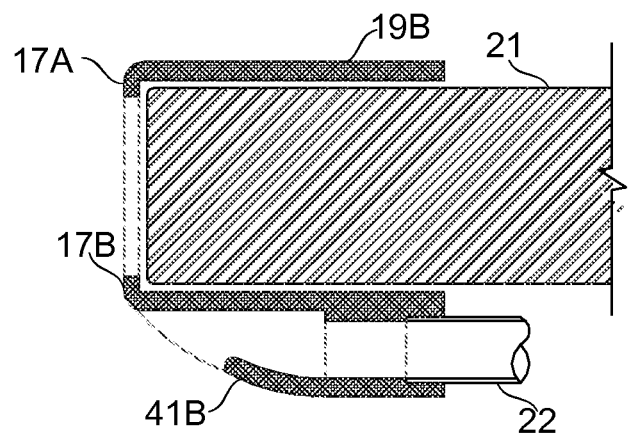

Reference is now made to FIGS. 8A-8C, which schematically illustrate an example of a tip adaptor 19B comprising an end-recessed intake guard 41B, according to some exemplary embodiments of the invention. FIGS. 8A-8B show frontal views at different section planes. FIG. 8C shows a view in horizontal cross-section.

In some embodiments, intake guard 41B is recessed away from the distal end of tip adaptor 19B. A potential advantage of this position is to protect of an evacuation lumen 22, with lowered obstruction of the progress and/or field of view of distal endoscope region 21. In particular, the extreme distal end of the advancing distal end is expanded only by the thickness of tip adaptor 19A used to house the anchoring structures of the adaptor. In some embodiments, one or more positioning elements 17A, 17B act to ensure proper relative positioning of tip adaptor 19A relative to the end of distal endoscope region 21.

Referring again to FIGS. 2A-2C, chamber 43 of tip adaptor 20 is for housing a distal end of an endoscope 21. A chamber 220 in the figure is for housing and/or connecting to (and functionally extending) a tube 22 which optionally connects proximally to a vacuum source as described above. Suction 71 produced by a proximal vacuum source is delivered in some embodiments by tube 22 and chamber 220 to an evacuation portal 95.

In some embodiments of the invention, tip adaptor 20 comprises a distal intake guard 41. Potentially, intake guard 41 serves to separate body lumen wall tissue or other body tissue from direct exposure to high levels of vacuum potentially present in an evacuation portal 95.

Figure 2D:
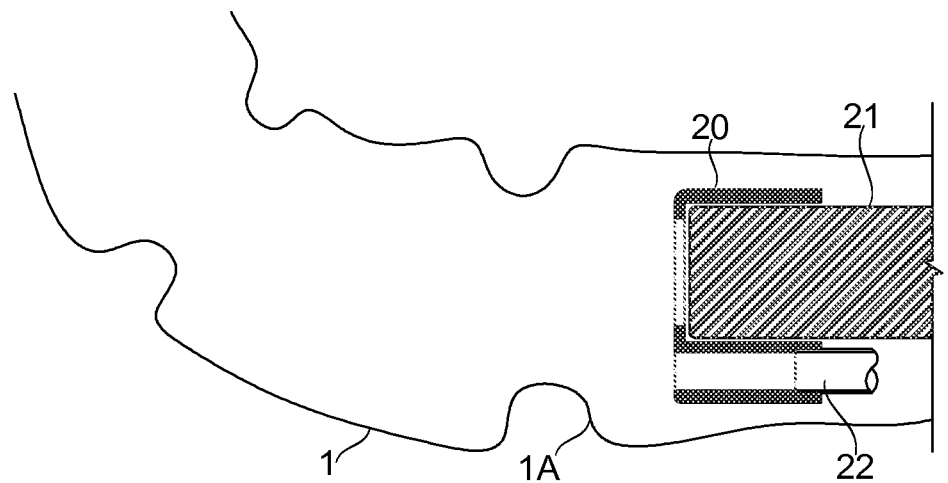
FIGS. 2D-2E show an encounter between a portion of an intestinal wall and vacuum pulled through an evacuation lumen of tip adaptor, according to some exemplary embodiments of the invention.
Figure 2E:
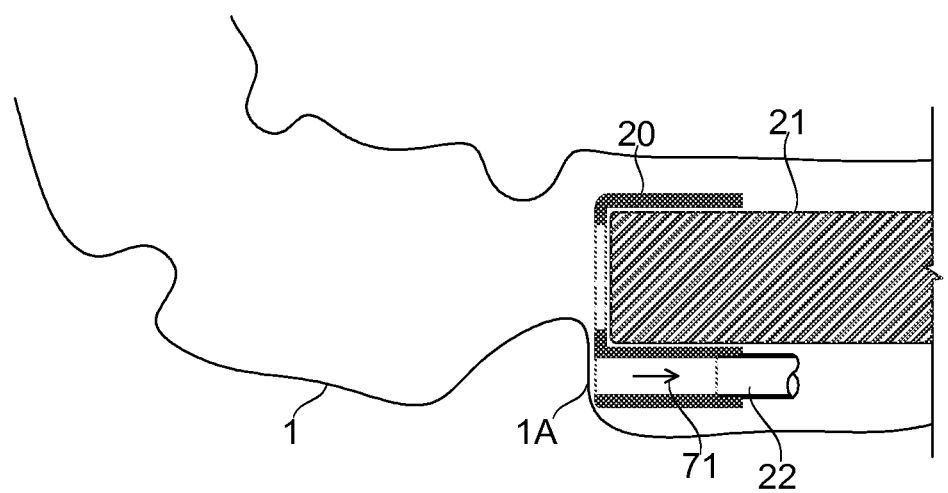

Reference is now made to FIGS. 2D and 2E, which show an encounter between a portion 1A of an intestinal wall 1 and vacuum pulled in direction 71 through an evacuation lumen 22 of tip adaptor 20, according to some exemplary embodiments of the invention. In FIG. 2D, an advancing distal end of an endoscope 21 approaches an irregularity 1A in wall 1. In FIG. 2E, irregularity 1A is pulled to the aperture of evacuation lumen 22. It is, however, a potential advantage to prevent this mode of contact between an active evacuation portal and soft body tissue. Faults which potentially occur in this scenario include:

body tissues sucked towards and into the evacuation portal blocking the portal, preventing proper functioning of a lumen-cleaning process; and traumatizing of body tissues sucked into the evacuation portal.

Suction strong enough to provide efficient and rapid evacuation of fecal matter from a colon (for example) is potentially strong enough to create hematoma, ruptured blood vessels, or other undesirable outcomes in tissue subject to a strong suction.

Figure 3A:
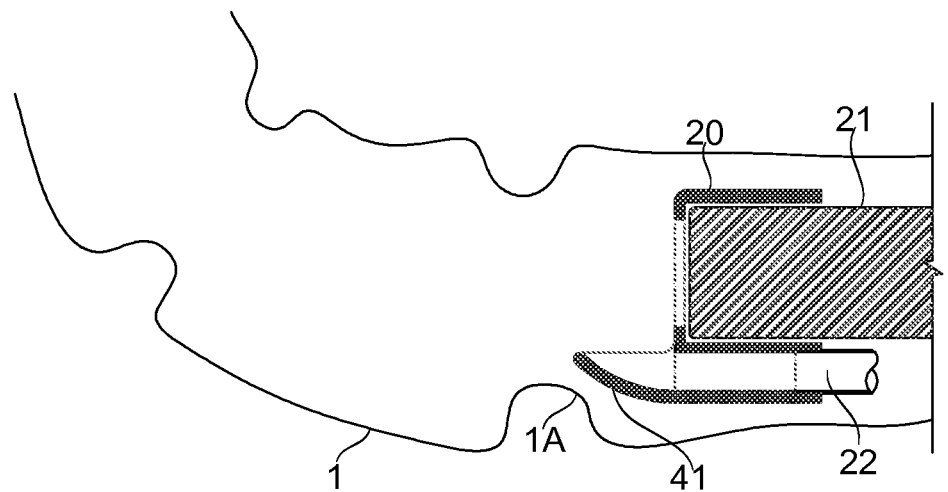
FIGS. 3A-3B show an encounter between a portion of an intestinal wall and vacuum pulled through an evacuation lumen of tip adaptor provided with an extension, according to some exemplary embodiments of the invention.
Figure 3B:
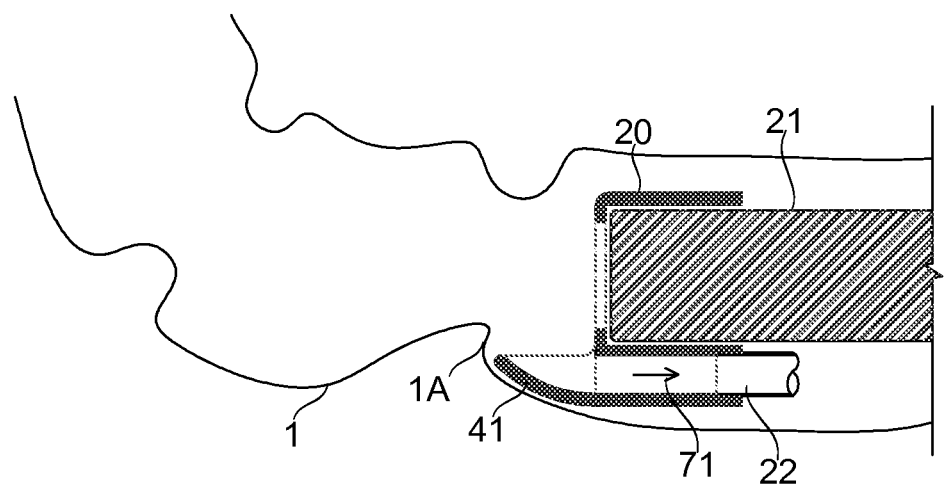

Reference is now made to FIGS. 3A and 3B, which show an encounter between a portion 1A of an intestinal wall 1 and vacuum pulled in direction 71 through an evacuation lumen 22 of tip adaptor 20, provided with an extension 41, according to some exemplary embodiments of the invention. In FIG. 3A, an advancing distal end of an endoscope 21 approaches an irregularity 1A in wall 1. In FIG. 3B, irregularity 1A is pushed forward, away from the aperture of evacuation lumen 22, protecting it from suction force 71.

Returning now to FIGS. 2A-2C, in some embodiments, extension 41 stands between evacuation portal 95 and sensitive tissue such as the wall of a colon, and protects that tissue from damage while preventing blockage of evacuation portal 95 by body tissue. In some embodiments, intake guard 41 is positioned near evacuation portal 95.

Optionally a plurality of shields 41 is positioned near a plurality of evacuation portals 95. Optionally, intake guard 41 is positioned around all or major portions of tip adaptor 20 and not be limited to positions in direct proximity to evacuation portals 95.

Optionally, intake guard 41 is curved towards a central axis of tip adaptor 20, as shown in FIG. 2C.

Figure 6A:
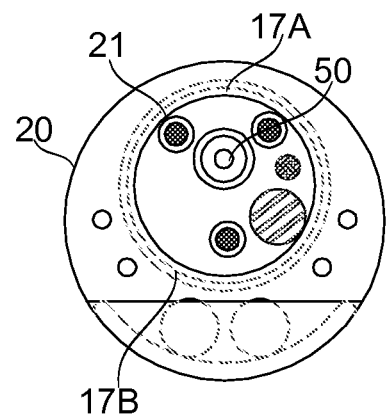
FIGS. 6A-6B illustrate a shield in relation to an imaging aperture, according to some exemplary embodiments of the invention.
Figure 6B:
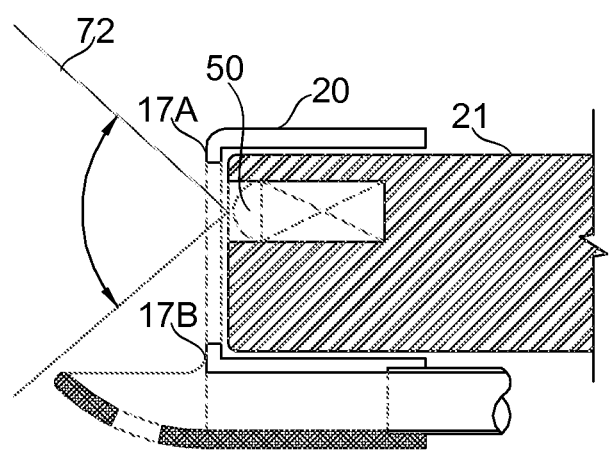

Reference is now made to FIGS. 6A-6B, which illustrate an intake guard 41 in relation to an imaging aperture 50, according to some exemplary embodiments of the invention.

Optionally, intake guard 41 is positioned to avoid or partially avoid limiting the field of view 72 of optical components of endoscope 10.

Figure 4A:
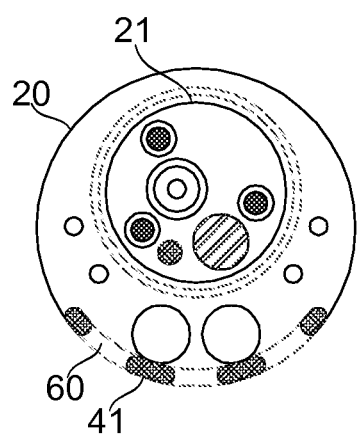
FIGS. 4A-4B schematically illustrate a tip adaptor which comprises a shield having at least one aperture, according to some exemplary embodiments of the invention.
Figure 4B:
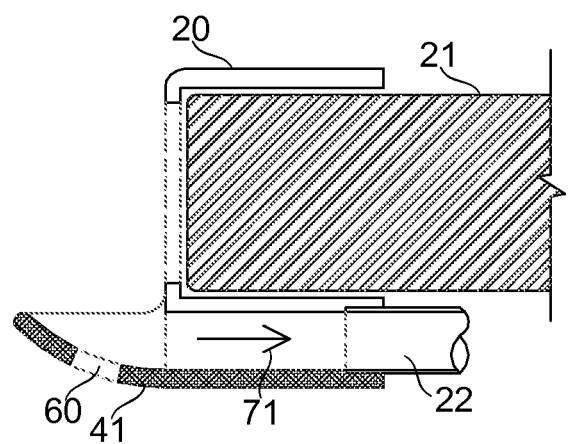

Reference is now made to FIGS. 4A-4B, which schematically illustrate a tip adaptor 20 which comprises an intake guard 41 having at least one aperture 60, according to some exemplary embodiments of the invention.

In some embodiments of the invention, intake guard 41 may comprise one or more (optionally small) holes 60 through which cleaning can occur. This configuration is shown in side cross-section in FIG. 4B and in front cross-section in FIG. 4A.

Optionally, holes 60 may have rounded edges so that they will not cut or scrape tissues of the lumen walls as tip adaptor 20 advances in the body lumen.

The appropriate size and location of holes 60 may depend on the characteristics of the material to be cleaned, the nature of the irrigation used, the strength of the suction provided, and various other operational parameters. FIGS. 4A and 4B present exemplary and non-limiting embodiments. In some embodiments, holes 60 are placed such that they overlie interior regions exposed to suction which experience a relatively small pressure differential with the intracolonic pressure. For example the holes may be placed near the distal end of an intake guard wall 41, and/or may be placed such that the nearest portion of the chamber formed on the interior side of the intake guard wall 41 is relatively large.

In some embodiments, this larger chamber region corresponds to an effectively increased "pipe" diameter, resulting in a lower pressure drop, for example according to Bernoulli's principle. This is a potential advantage for the safety of the tissue, and/or for reduction of the tendency of suction to grab approaching tissue.

In some embodiments, a potential tension exists within the goal of evacuating as much waste volume as practical, while exposing the tissues of the colonic segment to a pressure gradient which is as gentle as practical. In embodiments of this compromise, suction as such is not relied upon to dislodge particles. It is also a potential advantage to put apertures leading to the evacuation channel where they are exposed to the least pressure differential. It is another potential advantage for structures leading to the evacuation channel to have wide cross sections near such apertures, narrowing as they recede from regions which might be exposed to tissue.

According to some optional methods of use, a physician turns on suction in tube 22 when hole(s) 60 are appropriately positioned over an area needing cleaning, and turns off or reduces suction when holes 60 are positioned over vulnerable tissue.

Figure 5A:
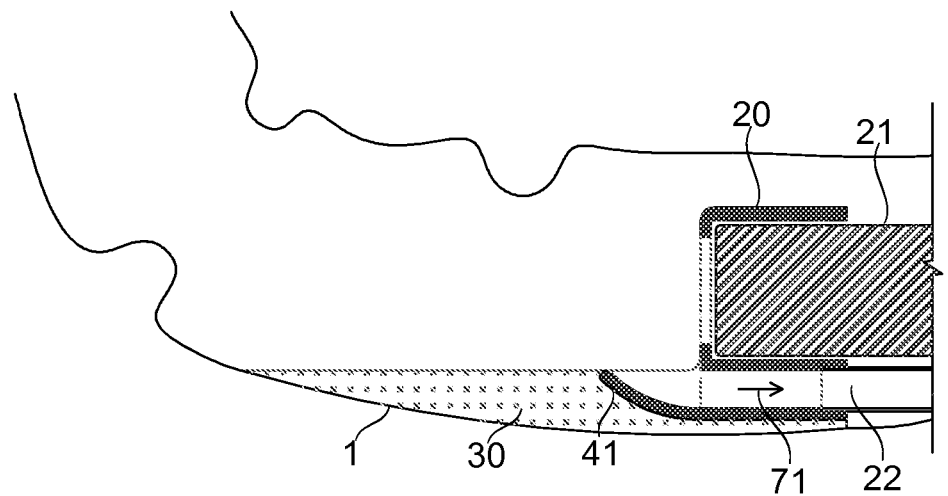
FIGS. 5A-5B illustrate drainage of fluid and suspended waste from an intestinal lumen, according to some exemplary embodiments of the invention.
Figure 5B:
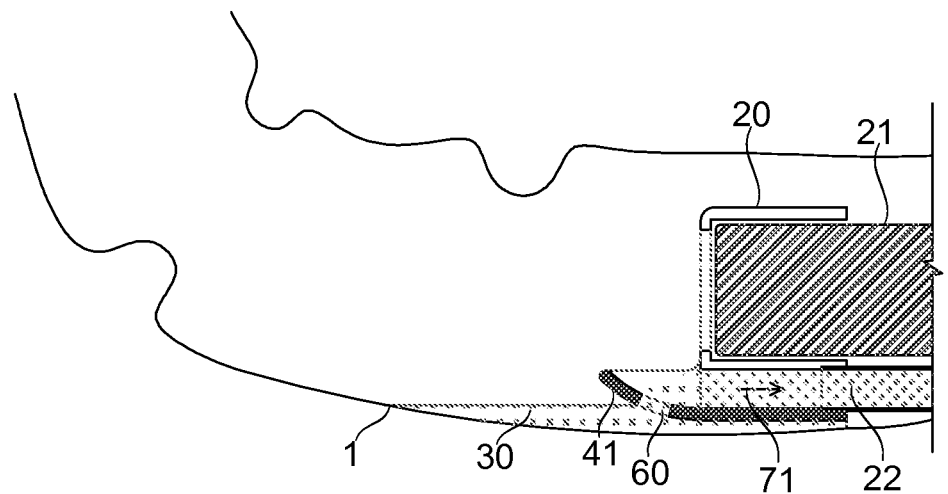

Reference is now made to FIGS. 5A and 5B, which illustrate drainage of fluid and suspended waste 30 from an intestinal lumen, according to some exemplary embodiments of the invention. In each figure, the lumen contained by intestinal wall 1 is being drained by vacuum pulled in direction 71 through an evacuation lumen 22 of tip adaptor 20, provided with an extension 41.

In FIG. 5A, a distal end of an endoscope 21 is partially submerged in fluid and suspended waste 30. Suction 71 is unable to completely drain waste suspension 30, due to the barrier comprising extension 41. In FIG. 5A, a distal end of an endoscope 21 is partially submerged in fluid and suspended waste 30. Suction 71 is provided access to remnants of drained waste suspension 30, by one or more holes 60 provided in extension 41.

Note that tip adaptor 20, in some embodiments, is configured to remain clear of colonoscope elements located at the colonoscope tip, comprising, for example (as shown in FIG. 2A), illumination LED 105, imaging port 107, working channel 102, and irrigation channel 103.

Exemplary Tip Adaptors

Reference is now made to FIGS. 11A-11D, 13A-13C, and 17A-17B, which schematically illustrate configurations for cleaning system 100 tip adaptors 20 mountable on distal portions 21 of endoscopes 10, according to some exemplary embodiments of the invention.

It is to be understood that, in some embodiments "tip adaptors" shown in these figures and referenced elsewhere herein are connectable to tubes 110 and to other portions of a cleaning system such as the cleaning system 100 of FIGS. 1A-1B.

It is also to be understood that configurations of what is generally referred to as "tip adaptor 20" herein should be understood to include (changed as necessary) all individually described tip adaptors described herein (for example, tip adaptors 11A-11C, 12, 13, and 19A-19B), and all other devices conforming to descriptions of "tip adaptors" presented herein as embodiments of the invention.

FIGS. 11A-11D schematically illustrate sectional side views of tip adaptors 11A-11C (and 20) mounted on a distal end of an endoscope 10.

In exemplary embodiments shown in FIGS. 11A-11C, tip adaptor 11A, 11B is shaped to fit the distal end of the endoscope, optionally with a fully or partially circumferential projection 16 or other feature which assures that tip adaptor 11A, 11B will be positioned at the distal end of endoscope 21 in a fixed positional relationship.

Figure 12A:
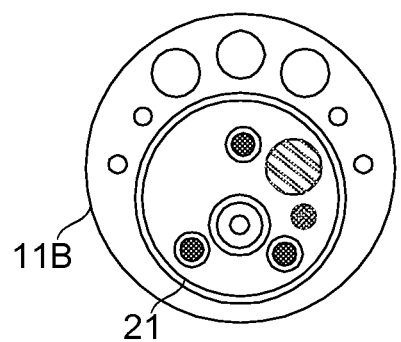
FIGS. 12A-12B show frontal and side-sectional views, respectively, of a tip adaptor in association with an endoscope distal end, according to some exemplary embodiments of the invention.
Figure 12B:
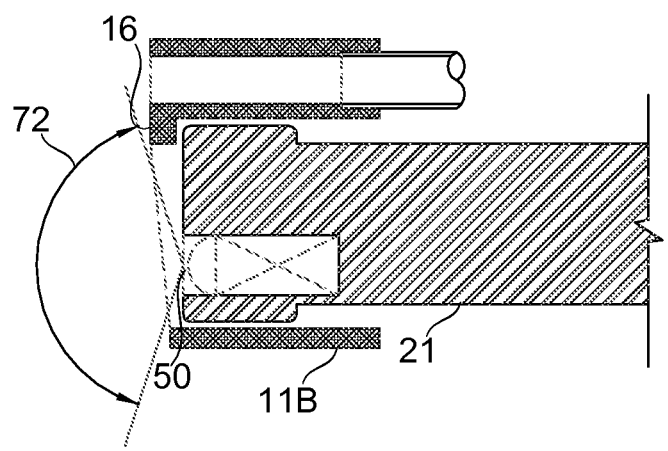

Reference is now made to FIGS. 12A-12B, which show frontal and side-sectional views, respectively, of a tip adaptor 11B in association with an endoscope distal end 21, according to some exemplary embodiments of the invention.

It is a potential advantage to adjust the shape of projection 16 to accommodate the function of features located at the end of distal endoscope portion 21. In some embodiments, for example, projection 16 may be retracted from portions of the tip adaptor 11B which are positionable in proximity to the field of view 72 of an imaging device 50. This retraction allows the positioning function to operate without impairing the functional operation of the endoscope optics and/or other features such as irrigation, working channels, and/or illumination.

FIGS. 11D, 13A-13C, and 17A-17B are simplified schematics of tip adaptors which are either variably positionable on distal portions of endoscopes 21, or which are fixedly positioned near but not at a distal end of an endoscope 21, according to some embodiments of the invention.

Figure 13A:
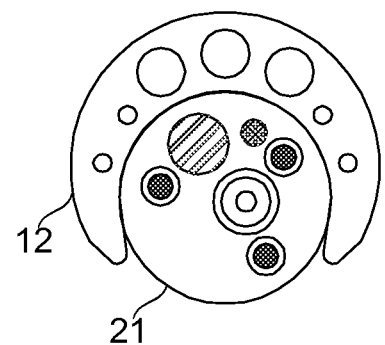
FIGS. 13A-13C schematically illustrate configurations for cleaning system tip adaptors mountable on distal portions of endoscopes, according to some exemplary embodiments of the invention.
Figure 13B:
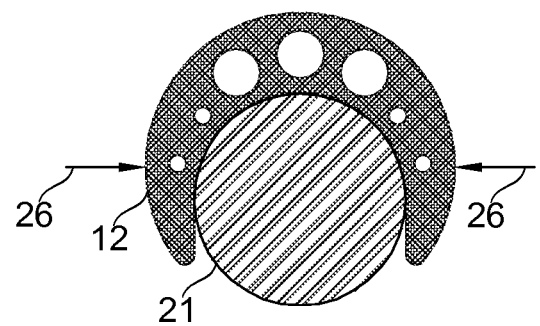
Figure 13C:
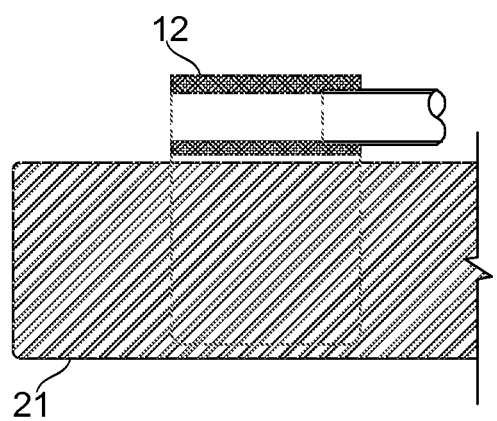

FIGS. 13A-C show front and front- and side-sectional views of tip adaptor 12 (which is a tip adaptor 20) configured to be fittingly applied over a distal portion of an endoscope 21 from a lateral direction. In some embodiments, interface tip adaptor 12 is elastically deformable, and sized to grip endoscope end 21 in a pressure grip (direction of grip pressure is indicated, for example, by arrows 26). Optionally, tip adaptor 12 is fitted by a user to a selectable position at or near the end of distal portion of endoscope 21. In some embodiments, tip adaptor 12, is optionally slideable for positioning along the distal body of endoscope 21. In some embodiments, tip adaptor 12 grips endoscope distal end 21 with a sufficient strength to resist movement on endoscope distal end 21 under influence of pressures normally exerted on endoscope 21 during insertion in a colon or other body lumen.

Figure 15A:
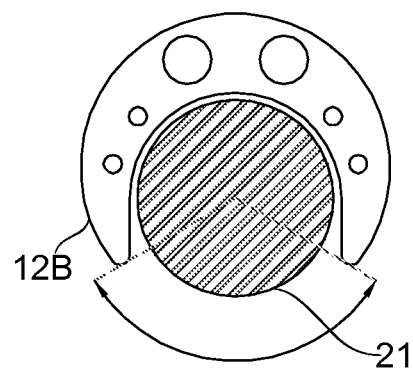
FIGS. 15A-15B schematically illustrate different circumferential extents of elastically deformable tip adaptors, according to some exemplary embodiments of the invention.
Figure 15B:
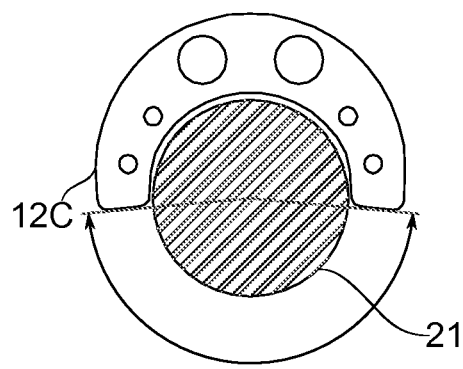

Reference is now made to FIGS. 15A-15B, which schematically illustrate different circumferential extents of elastically deformable tip adaptors 12B, 12C, according to some exemplary embodiments of the invention.

In some embodiments, the circumferential extent of a tip adaptor 12B, 12C is any angle sufficient to allow a grip to be established from behind the endoscope distal portion 21 to which the tip adaptor attaches. In some embodiments, the angle is also chosen so that the adaptor can be opened wide enough to pass over the endoscope portion 21 from the side.

In some embodiments, for example, tip adaptor 12B (FIG. 15A) extends around about ⅔ of the circumference of the endoscope. It should be understood that the extent of circumferential wrapping is variable, depending on the diameter of the endoscope at the point of attachment.

In some embodiments, for example, tip adaptor 12C (FIG. 15B), extends only a small amount past 180° of the endoscope circumference at the point of attachment. In some embodiments, the security of attachment is increased by decreasing the flexibility of the tip adaptor 12C, such that the pressing to the underlying endoscope is harder.

Thus, in some embodiments, tip adaptors which self-attach by means of their own elastic restoring force may be constructed with a relaxed-state aperture which is anywhere in size from 0% of the endoscope diameter (slit-like) to a value just sufficiently small enough allow establishing a grip. The relaxed-state aperture size may thus be, for example, 20%-80% of the endoscope diameter, or another larger or smaller size. In some embodiments, the adaptor extends from fitting about 50% around the endoscope probe profile to any larger value. A more completely enclosing adaptor potentially provides a firmer grip, with a trade-off for this comprising a larger increase in endoscope probe diameter.

The material of the tip adaptor body (for adaptors 12B, 12C, or any other tip adaptor described herein) can be a silicone rubber or another polymer material, for example, a polymer resin otherwise used in manufacture of a colonoscope or colon cleaning system insertion tube. Exemplary Shore A durometer values for the material of a tip adaptor are between 50-70 Shore A durometer units. In some embodiments, a Shore A durometer range of 50-55 Shore A, 50-60 Shore A, 55-65 Shore A, 70-80 Shore A, 70-90 Shore A, or another range of durometer having bounds equal, intermediate, higher or lower is used.

In some embodiments, a transparent material is used to form a tip adaptor (for example, tip adaptor 12B, 12C, or any other tip adaptor described herein). A potential advantage of transparency is more direct determination of the positioning of the adaptor on the colonoscope end.

Figure 16A:
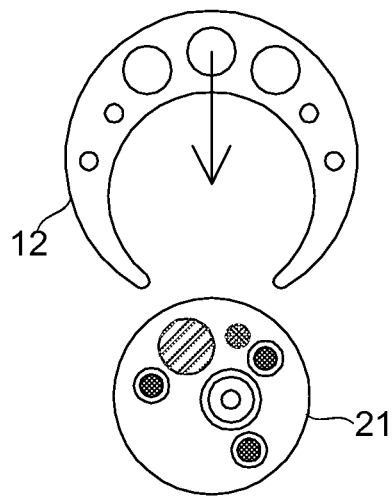
FIGS. 16A-16C illustrate an elastically deformable tip adaptor in three configurations relative to a distal portion of an endoscope, according to some exemplary embodiments of the invention.
Figure 16B:
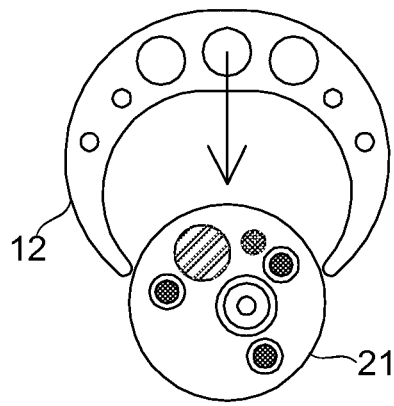
Figure 16C:
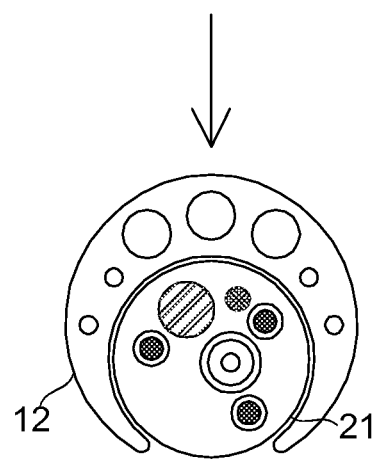

Reference is now made to FIGS. 16A-16C, which illustrate an elastically deformable tip adaptor 12 in three configurations relative to a distal portion of an endoscope 21, according to some exemplary embodiments of the invention. Configurations shown are pre attachment (FIG. 16A), mid-attachment (FIG. 16B), and after attachment (FIG. 16C). The sequence illustrates the flexibility of adaptor 12 for insertion over an endoscope from the side, and its capability for attachment by shape restoration once pressed onto an endoscope tube.

In some embodiments, a position for tip adaptor 20 with respect to a distal end of endoscope 21 is selected by a user according to preference and/or according to a given clinical situation, and tip adaptor 20 attached to endoscope distal end 21 according to the position selected. In some embodiments, tip adaptor 20 and/or attached tubes 110 are disposable objects intended for one-time use.

In some embodiments, distal interface 20 is fixedly connected to an endoscope distal region 21 at a position proximally spaced from the end itself (FIG. 13C). The distance is at least, for example, 0.5-1.5 cm, 1-2.5 cm, 2-5 cm, or a shorter or longer distance from the distal end of the endoscope.

A potential advantage of the configurations shown in FIGS. 13A-13C and 17A-17B is ensuring the optics of endoscope 10 a full field of view. If tip adaptor 20 is positioned near the end of endoscope 21 but is somewhat distanced from that end, then even unusually large tip adaptors may not interfere with full field of view for the endoscope optics.

In some methods of use in some embodiments, an endoscope 10 with attached cleaning system 100 is advanceable throughout a length of a colon with the cleaning to system in use during the advance, so that the cleaning system cleans fecal matter from the length of colon. Optionally, the endoscope is subsequently gradually retracted through the cleaned colon for inspection and/or treatment. Under this method, the fact that tip adaptor 20 is positioned proximally to the distal end of the endoscope is convenient both during advancing/cleaning and during retracting/observing. During advancing, potentially, the distal tip is more easily able to penetrate restricted spaces, in virtue of not having to support the added bulk of the adaptor tip at the point of penetration. During retraction, potentially, the adaptor tip is clear of interfering with illumination and/or imaging elements in virtue of being physically out of their field of illumination and/or view.

Figure 17A:
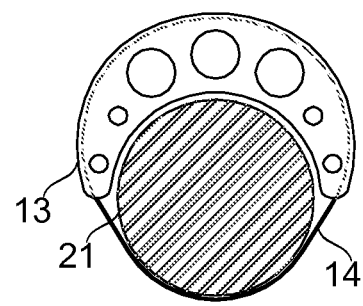
FIGS. 17A-17B schematically illustrate configurations for cleaning system tip adaptors mountable on distal portions of endoscopes, according to some exemplary embodiments of the invention.
Figure 17B:
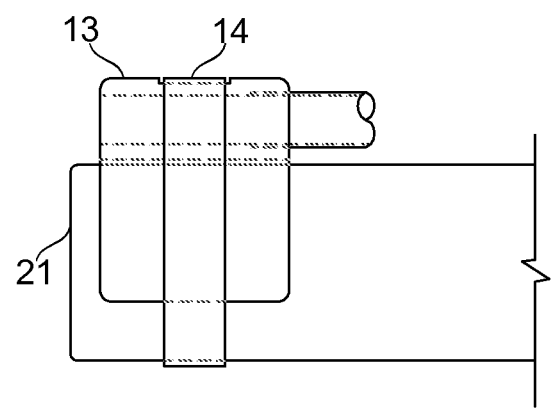

FIGS. 17A-17B exemplify (in frontal and side views) a tip adaptor 13 which mounts on an endoscope 21, optionally from the side of the endoscope, and is in contact with or in proximity to a distal portion of endoscope 21 along a portion (for example, about 40% or about 50% or about 60% or about 70% or about 80%) of the endoscope circumference. In some embodiments, it does not surround as much as 50% of its circumference. In some embodiments, interface tip adaptor 13 is attachable at a variety of positions along a distal portion of endoscope 21. Optionally, tip adaptor 13 is held in place by an attachment 14 such as a bonding tape, clamp and/or any other mechanical, bonding, and/or gluing means; a strap, and/or by attachments 112 along connecting tubes 110, themselves connected to tip adaptor 13 along the length of endoscope 10 as described above with reference to FIGS. 1A-1B.

In some embodiments, interface tip adaptors 12 and 13 are positionable anywhere on the distal portion of endoscope 21, to suit a physician's convenience and/or to suit the clinical requirements of a particular case. It is a potential advantage of tip adaptors having flexible and/or side-attachable, tip adaptor 13 that they are attachable for use with endoscopes of a variety of shapes and/or diameters. In some embodiments, tip adaptor 13 is constructed of elastically flexible material to further make it adaptable to endoscopes of varying sizes. For similar reasons, tip adaptor 13 is optionally adaptable to being mounted on a portion of distal endoscope 21 having a non-circular or asymmetrical cross-section.

Embodiments shown in FIGS. 11D, 13A-13C, and 17A-17B are optionally usable to position distal outlets of "cleaning tubes" (that is, one or more irrigation tubes and/or one or more evacuation tubes) at a user-selected position with respect to a distal end of an endoscope.

Reference is now made to FIGS. 10A-10D, which illustrate over-the-end attachment of an adaptor tip 20 to an endoscope distal end 21, according to some exemplary embodiments of the invention.

In some embodiments, tip adaptor 20 is attachable over the end of endoscope distal region 21 (FIG. 10B) to a range of positions relative to the distal end. The position may be flush or nearly flush with the end (FIG. 10C), or it may be offset proximally by a distance 28, for example, 0.5-1.5 cm, 1-2 cm, 1.5-3 cm, or another longer or shorter offset length.

Reference is now made to FIGS. 9A-9D, which illustrate a problem related to attachment of an adaptor tip 20 to an endoscope distal end 21 having variable diameter, according to some exemplary embodiments of the invention.

Figure 9A:
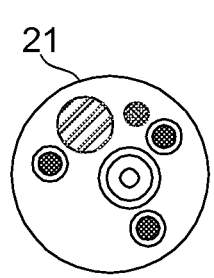
FIGS. 9A-9D illustrate attachment of an adaptor tip to an endoscope distal end having variable diameter, according to some exemplary embodiments of the invention.
Figure 9B:
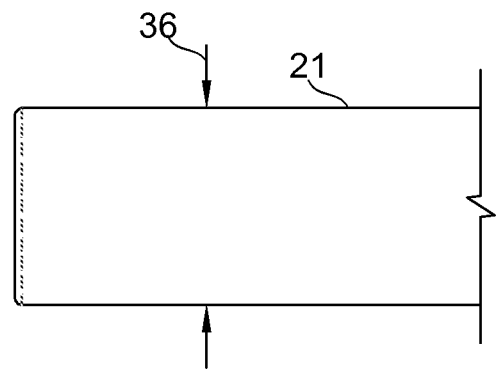
Figure 9C:
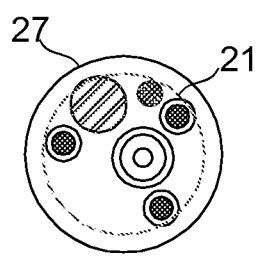
Figure 9D:
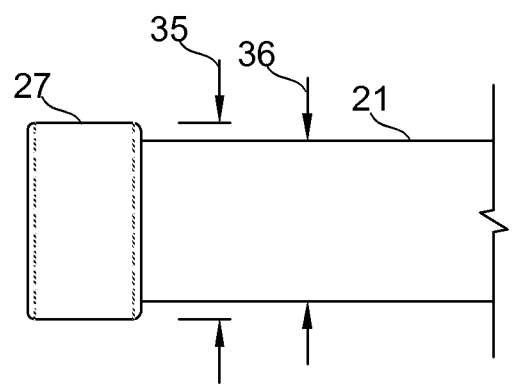
Figure 10A:
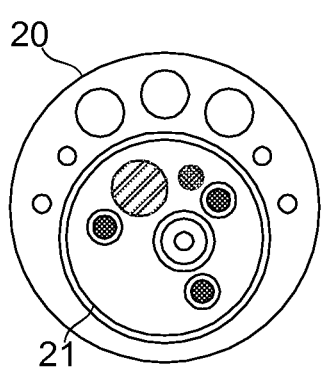
FIGS. 10A-10D illustrate over-the-end attachment of an adaptor tip to an endoscope distal end, according to some exemplary embodiments of the invention.
Figure 10B:
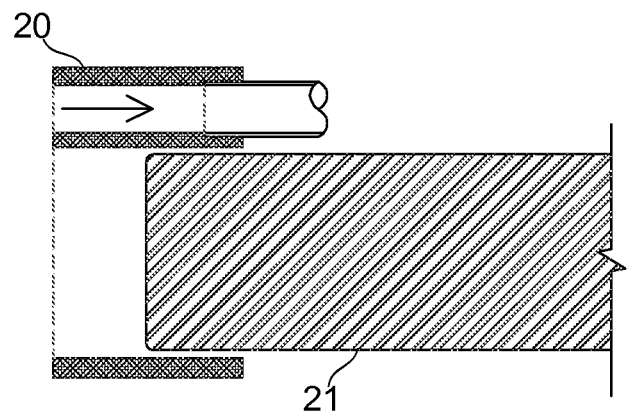
Figure 10C:
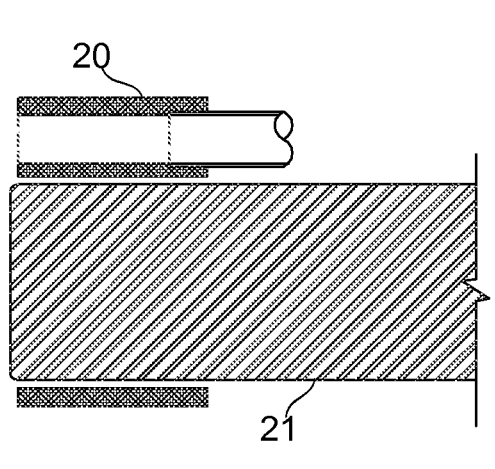
Figure 10D:
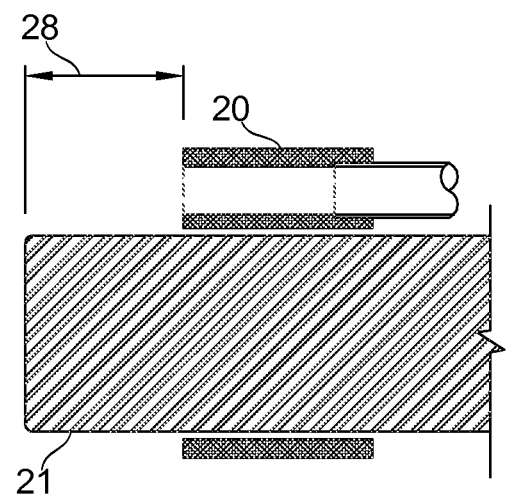

In some embodiments, an endoscope distal portion 21 comprises a relatively uniform diameter 36 extending proximally from the endoscope distal end (FIGS. 9A-9B). In some embodiments of the invention, the endoscope distal portion is not of uniform diameter, as shown here, but may comprise irregularities, for example, due to endoscope wrapping, steering mechanism, and/or other structures. The segmented appearance of endoscope distal portion 21 in FIGS. 1A-1B reflects these irregularities. It should be noted that it is a potential advantage of elastically deformable embodiments, for example, those of FIGS. 13A-13C, that they potentially adjust to such irregularities automatically.

In some embodiments, the irregularity is sufficiently large as to pose an obstacle to fitting an adaptor tip 20 over the distal portion. For example, the diameter 35 of expanded region 27 (FIGS. 9C-9D) is larger than diameter 36, so that an over-the-end, form-fitting attachment proximal to the distal end of endoscope distal region 21 is impeded.

Figure 14A:
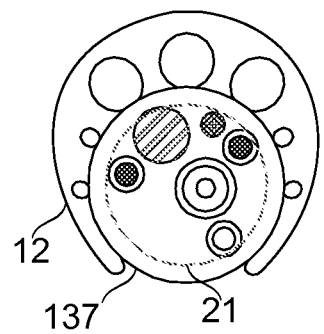
FIGS. 14A-14C demonstrate attachment of a tip adaptor to an endoscope probe comprising an expanded distal portion, according to some exemplary embodiments of the invention.
Figure 14B:
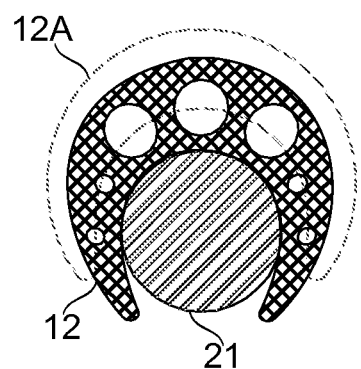
Figure 14C:
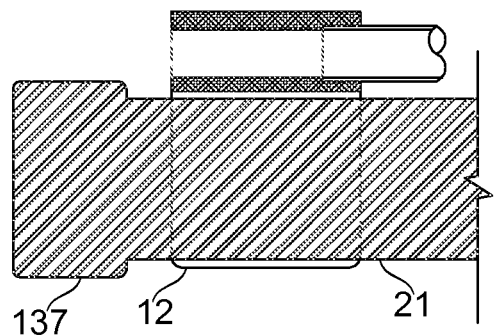

Reference is now made to FIGS. 14A-14C, which demonstrate attachment of a tip adaptor 12 to an endoscope probe comprising an expanded distal portion 27, according to some exemplary embodiments of the invention.

In some embodiments, endoscope distal region 21 is constructed with an expanded region 27, for example a ring 137 encircling the distal end. Ring 137 or other expanded region 27 may be provided to fulfill functional needs of endoscopes 21, for example to accommodate manipulating tools, illumination, and/or imaging optics. Nevertheless, such expansions potentially interfere with the navigability of an endoscope end. While sufficient care may have been taken in the design of the original endoscope to preserve maneuverability, adding a tip adaptor 20 that further enlarges the distal end of an endoscope 21 is potentially detrimental to successful navigation through a colon.

A tip adaptor such as 12 or 13 attachable to an endoscope 21 at a position proximal to an expanded distal potentially allows a narrower profile of the tip adaptor and endoscope combination. Potentially, a narrower profile is more navigable. In FIGS. 14A-14C, for example, a tip adaptor 12 is shown attached at a region proximal to an expansion 27, permitting a profile which is within a profile 12A which the same adaptor would assume if placed directly over the expansion 27 of the endoscope distal end 21.

Figure 15C:
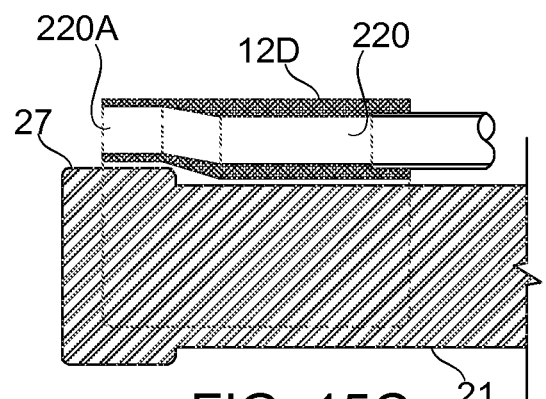
FIG. 15C shows an extension of housing area of a tip adaptor over a distal end expansion, according to some exemplary embodiments of the invention.

Reference is now made to FIG. 15C, which shows an extension 220A of housing area 220 of a tip adaptor 12D over distal end expansion 27, according to some exemplary embodiments of the invention.

In some embodiments, tip adaptor 12D is configured to attach distally to the end of distal endoscope region 21, with a short extension 220A, configured to rise over an expanded region 27 and project forward, bringing an aperture of an evacuation channel 95, for example, further forward while the main body of the tip adaptor 12 remains at a more sheltered proximal position.

Reference is now made to FIG. 11D, which shows an over-the-end applied tip adaptor 11C, associated with an endoscope distal portion 21, according to some exemplary embodiments of the invention.

A potential advantage of side-mounting tip adaptors is seen by comparison of FIG. 11D with FIG. 14C. In FIG. 11D, the adaptor 11C is separated by a distance 28 from the distal end of endoscope 21, after sliding over a distal expansion 27. However, the resulting configuration is not well fitted, and has excessive diameter relative to the diameter achievable with a configuration such as that of FIG. 14C. Even in the case of an over-the-end configuration mounted more securely at the distal end, as in FIG. 11C, the tip adaptor 11B is potentially more obstructive than the configuration of FIG. 14C.

Figure 19A:
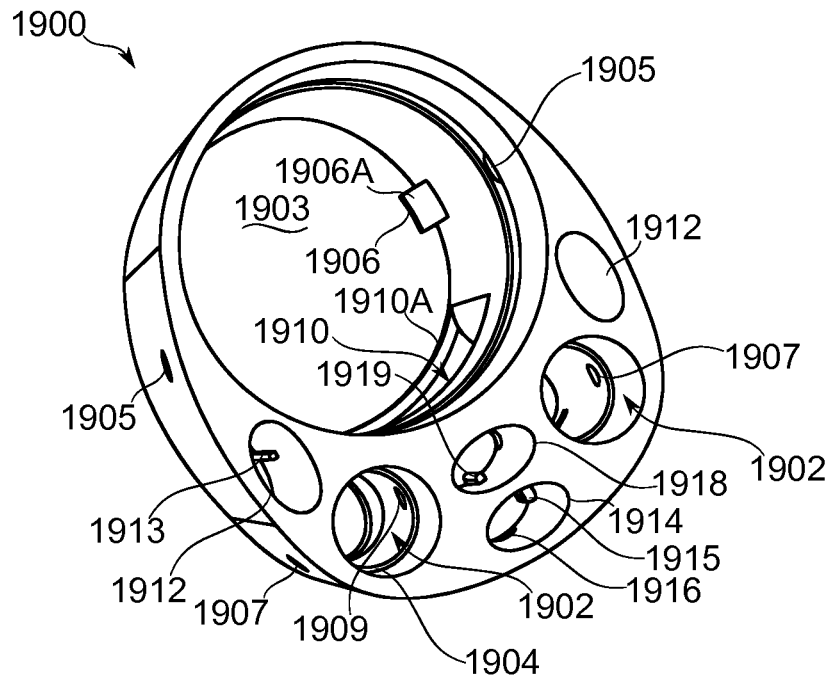
FIGS. 19A-19C schematically illustrate a tip adaptor comprising an evacuation antechamber, according to some exemplary embodiments of the invention.
Figure 19B:
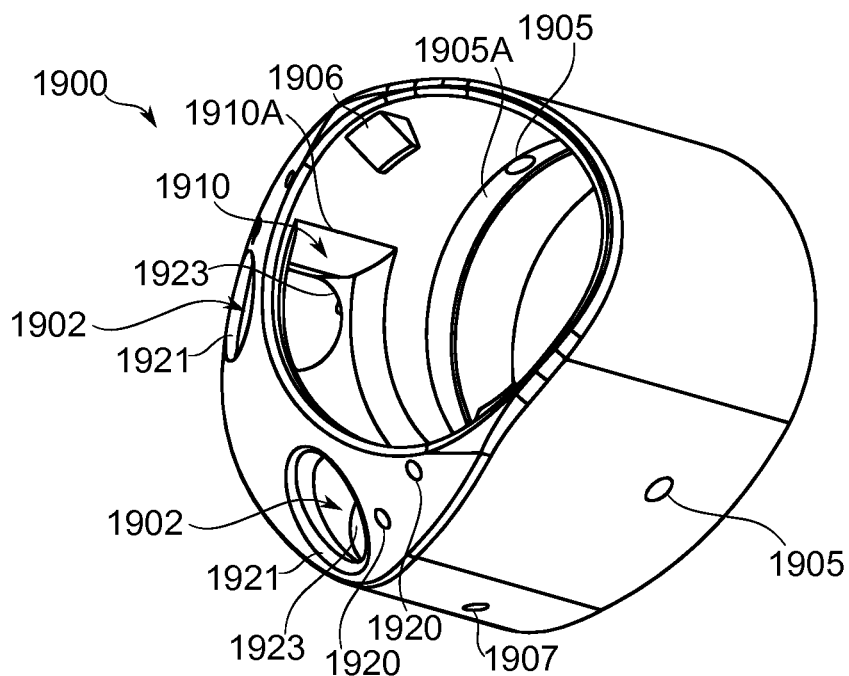
Figure 19C:
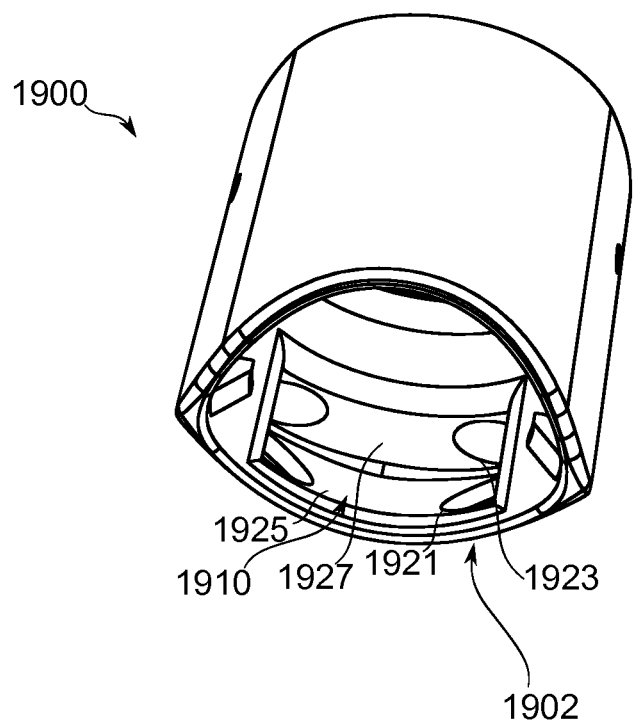

Reference is now made to FIGS. 18A-18C, which schematically illustrate a tip adaptor 1800 comprising a shell 1801 and an insert 1805, according to some exemplary embodiments of the invention. In some embodiments, the shell is relatively soft, and the insert is relatively hard. In some embodiments, the insert is relatively soft, and the shell is relatively hard. The two alternative configurations potentially provide alternative sets of benefits, as described hereinbelow. Reference is also made to FIGS. 19A-19C, which schematically illustrate a tip adaptor 1900 comprising an evacuation antechamber 1910, according to some exemplary embodiments of the invention.

In some embodiments of the invention, a tip adaptor 1800, 1900 comprises a colonoscope mounting lumen 1903, sized and shaped to receive the distal end of a colonoscope. Optionally, the tip adaptor 1800, 1900 also comprises:
  one or more evacuation channel mounting sockets 1902 for tubes of the evacuation channel,
  one or more irrigation channel mounting sockets 1912 for tubes providing irrigation fluid, and/or
  one or more pressure sensor sockets 1918, 1914 for receiving pressure sensing means.

In some embodiments of the invention, an evacuation socket 1902 comprises structures related to the assembly, sensing, safety, and/or blockage resistance of the evacuation channels of a colon cleaning device tip adaptor.

In some embodiments, the distal end of the tube of an evacuation channel 22 inserts into the proximal side of an evacuation channel mounting socket 1902. Optionally, it is secured by a friction fit and/or adhesive. Optionally, the depth of tube insertion is limited by a tube stop 1904, which comprises a partial restriction within the lumen of evacuation socket 1902. The partial restriction is optionally a circumferential narrowing of socket 1902. Optionally, the stop comprises a non-circumferential raised portion of the lumen wall.

Distal to the tube stop, in some embodiments, an evacuation channel tip pressure sensing aperture 1909 is provided. Optionally, the pressure sensing aperture comprises a lumen extending between evacuation channel mounting socket 1902, and pressure sensor socket 1918. In some embodiments, a hole 1907 is provided opposite the sensing aperture hole 1909 in the wall of evacuation socket 1902. The hole 1907 is optionally created during the process of manufacture to provide access for the creation of hole 1909.

Additionally or alternatively, it serves as a secondary suction relief aperture.

In some embodiments, socket 1902 terminates at a distal evacuation socket aperture 1923, leading into evacuation antechamber 1910. As such, socket aperture 1923 also comprises the intake aperture 95 of the evacuation channel.

Optionally, a proximal wall 1927 of evacuation antechamber 1910 comprises one or more such distal evacuation socket apertures 1923. In some embodiments, a distal wall 1925 of evacuation antechamber 1910 comprises one or more evacuation antechamber access apertures 1921. Optionally, evacuation antechamber 1910 comprises another aperture 1910A, across which lumen 1903 is in fluid communication with antechamber 1910.

In some embodiments, the structures forming antechamber 1910 and its apertures comprise functions described also, for example, in relation to FIGS. 3A-5B, and/or 7A-7C. For example, distal wall 1925 comprises an intake guard 41, insofar as it enforces a separation of the intestinal wall 1 from socket aperture 1923. Evacuation antechamber access aperture 1921 comprises an embodiment of an aperture or hole 60 which allows passage of sufficiently small material therethrough.

Potential advantages of the structure of antechamber 1910 and its apertures can be considered in terms of the pressures experienced by different sizes of granulated waste material as it passes into the antechamber 1910, and thence into one of the evacuation intake apertures 1923. With the evacuation channel side of the cleaning probe oriented to down (as in, for example, FIGS. 5A-5B), fluid level is readily reduced to a low depth, as the access apertures 1921 are positioned low on the tip head, and a sufficient pressure gradient is generated by suction from the evacuation channel 22 across access apertures 1921 to move fluid volume.

Optionally, access apertures 1921 are sized to be no larger than intake apertures 1923. Optionally, access apertures 1921 are positioned axially distal to intake apertures 1923. A potential advantage of this is that it helps ensure that an oblate waste particle entering access aperture 1921 is oriented to enter the evacuation channel, rather than block across it. In this sense, access aperture 1921 potentially acts as a waste particle strainer. In cases where waste particles are too large, and/or improperly oriented to pass into an access aperture 1921, the waste particle is nevertheless less likely to become suction-impacted within the access aperture 1921, as the pressure gradient is relieved by one of the other antechamber apertures 1921, 1910A, 1907. Aperture 1910A, by being relatively elevated, and at a relatively protected position within lumen 1903, is less likely to encounter large particles for which pre-straining is an advantage. Optionally, however, aperture 1910A is divided into two or more smaller apertures, potentially also providing a straining function for the intake aperture 1923.

Figure 23:
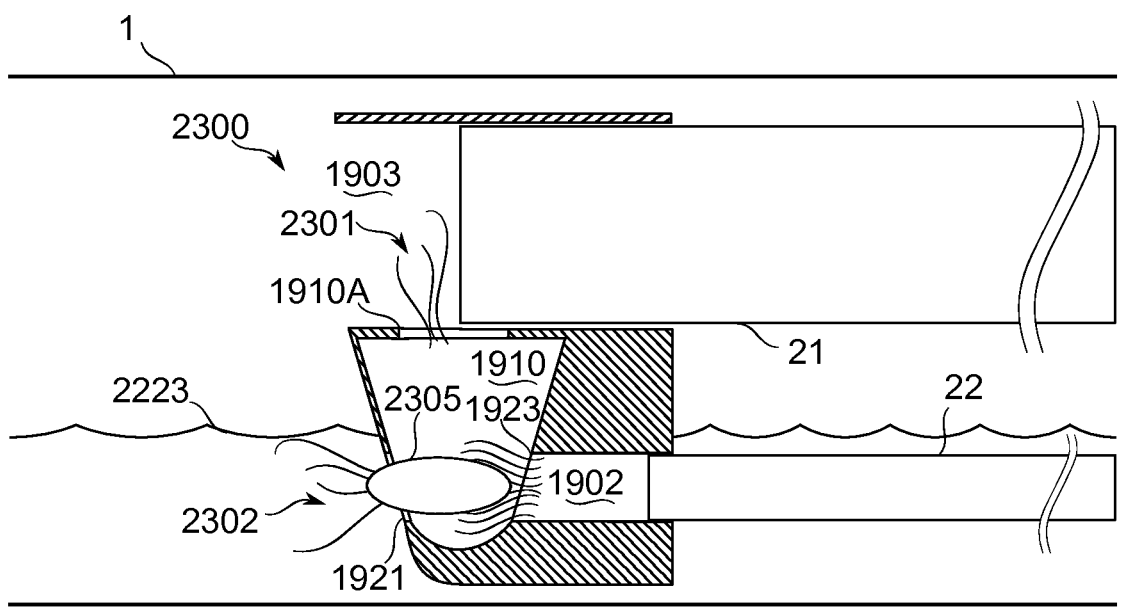
FIG. 23 schematically illustrates a particle entering a distal tip adaptor, according to some exemplary embodiments of the invention.

Reference is now made to FIG. 23, which schematically illustrates a particle 2305 entering a distal tip adaptor 2300, according to some exemplary embodiments of the invention.

In some embodiments, a tip 2300 (simplified to emphasize aspects related to evacuation antechamber 1910) is attached to a colonoscope probe 21 within lumen 1903, and an evacuation channel 22 at evacuation socket 1902. Suction is actively applied to the evacuation channel 22 such that material entering antechamber 1910 is evacuated. In some embodiments, this creates additional suction gradients 2301, 2302 from apertures 1910A and 1921, respectively. When waste (fluid with suspended solids) level 2223 is positioned about at or above aperture 1921, waste is pulled into the antechamber. If resistance at this aperture rises, however, the corresponding rise in the steepness of the pressure gradient is reduced by suction relief action of aperture 1910A. Resistance can rise, for example, upon encountering a portion of intestinal wall 1, for example as shown in relation to FIGS. 2D-2E. Potentially, shunting of the pressure gradient acts to reduce an incidence of suction-related injury. Particle 2305 represents a waste particle which, though large in one dimension, has been aligned to by passage through aperture 1921 so that it can enter channel 22 rather than being jammed to across intake aperture 1923.

In some embodiments, the provision of pluralities of apertures provides a further functional advantage. If a single access aperture 1921 becomes blocked, for example, it is nevertheless possible for a plurality of evacuation intake apertures to continue receiving fluid from the common antechamber 1910 fed by another access aperture 1921.

A further functional aspect related to evacuation antechamber 1910 is the rounded shaping of the distal wall 1925 such that while it provides separation of regions experiencing a steep pressure from the intestinal wall 1, it also presents a blunted front aspect 1802. Potentially, this reduces mechanical damage from poking, cutting, catching, and/or slicing. Insofar as the rounded tip shape is also tapering, the chances of catching are potentially reduced, as the shape of the tip encourages sliding away from and over wall obstructions, rather than bluntly pushing at them. Potentially, rounded shaping of the whole of the front surface ("spherical" shaping, though it need not be actually a section of a spherical surface) also reduces the likelihood of catching on walls by suction grip, by presenting inlet aperture shapes to which the intestinal wall 1 is not well suited to simultaneously conform (and block).

Another aspect of distal tip 1800, 1900 relates to the structures associated with colonoscope mounting lumen 1903. In some embodiments, a colonoscope stop 1906 is provided, which protrudes into the lumen 1903 such that the placement of the cleaning tip 1800, 1900 on the colonoscope distal end is precisely limited to the point at which the colonoscope contacts stopping surface 1906A. It is a potential advantage, for example, if the colonoscope end is prevented from blocking antechamber aperture 1910A.

Reference is now made to FIG. 21, which schematically illustrates a sleeve assembly 2104 in a sleeve placement jig 2100 together with components of an irrigation system and a colonoscope 21, according to some exemplary embodiments of the invention.

In some embodiments of the invention, tip 1800, 1900 is attached to one end of a thin-walled, flexible sleeve of a polymer (such as polyurethane, silicone rubber, or another flexible polymer) which is sized to fittingly accommodate and/or fair the colonoscope and/or other tube elements which comprise the fully assembled cleaning apparatus. Potential advantages of the sleeve assembly 2104 include: allowing reversible attachment of the cleaning apparatus to a colonoscope (for example, so that the cleaning apparatus can be exchanged and/or disposed of after use); ease of integration of a cleaning system with a colonoscope probe, and/or reproducible control of the integrated cleaning system/colonoscope probe system configuration shape and relative positioning.

In some embodiments, the sleeve assembly comprises an inner sleeve 2103, adapted for receiving a colonoscope probe 21. Inner sleeve 2103 is circumferentially surrounded by an outer sleeve 2102, including one or more add-on tubes 21, 101.

In some embodiments, a diameter of a lumen of inner sleeve 2103, in a non-expanded state, ranges between, for example, 8-12 mm, 3-10 mm, 5-18 mm, or another range having the same, intermediate, larger and/or smaller bounds. Optionally, the diameter is selected according to a diameter of a colonoscope; for example, 5%, 10%, 20% or an intermediate, larger or smaller percentage smaller (before stretching) than a diameter of a colonoscope. As particular examples: for a colonoscope having a diameter of 12 mm, the inner diameter is smaller than the colonoscope's diameter in a non-expanded state by 0.1-5 mm, 1-3 mm, 0.1-0.9 mm or another range of sizes having the same, intermediate, larger and/or smaller bounds.

In some embodiments, sleeve assembly 2104 is inflatable for receiving a colonoscope probe by attachment to an inflation base 2107 of inflation jig 2100, the base 2107 comprising an inflation inlet 2105 configured to be attached to a gas pressure source for inflation. Optionally, an inflation jig 2100 comprises a restriction tube or partial tube 2101, though which sleeve assembly 2104 is extended for receiving a colonoscope probe 21. Colonoscope probe 21 is optionally inserted through sealing member 2106, and fed through the inner sleeve 2103 until reaching lumen 1903 of the distal tip 1900.

Optionally, the flexible sleeve is secured by a circumference around attachment channel 1905A. Optionally, the sleeve comprises an outer tube and at least one inner tube; optionally, the inner tube is attached to attachment channel 1905A. Optionally, adhesive introduction aperture 1905 is provided, leading from the outside of the tip leading to lumen 1903 and attachment channel 1905A. Optionally, the fairing tube is secured to channel 1905A by placement of one end within lumen 1903 and pressing against channel 1905A, followed by adhesive injection all around the lumen. Returning to FIGS. 18A-19C, in some embodiments of the invention, irrigation channel 101 terminates at tip 1800, 1900 by insertion into an irrigation tube receiving socket 1912. Optionally, socket 1912 is elongated to allow two or more separate irrigation tubes to insert alongside each other. Optionally, insert depth into the socket is set by one or more irrigation tube stops 1913. In some embodiments, one or more irrigation outlets 1920 are provided for each socket 1912. Optionally, the irrigation outlets 1920 comprise cylindrical holes oriented along the distal-proximal axis of the tip body. Optionally, the irrigation outlets 1920 are otherwise shaped and/or oriented for jetting—for example, comprising a tapered lumen, and/or aimed off the distal-proximal axis for distributing and/or aiming the irrigation fluid spray.

In some embodiments of the invention, sensor sockets 1918, 1914 are configured to receive sensing probe and/or sensing probe portions, to allow one or more aspects of the tip and/or tip environment to be sensed. For example, evacuation lumen pressure sensor socket 1918 is optionally provided with a sensor which is linked through sensing aperture 1909 to one or more evacuation sockets 1902 for sensing of pressure and/or pressure changes therein. In some embodiments, an electronic pressure sensor is provided. In some embodiments, a mechanical pressure sensor is provided. For example, a pressure sensor optionally comprises a fluid-filled tube to which a test pressure is proximally applied. As pressure at the distal tip rises and/or falls, the volume moved by the test pressure changes, which is optionally transduced into a measurement and/or indication of distal tip pressure.

In some embodiments, external pressure sensor socket 1914 is configured to receive a pressure sensor which senses an external pressure through external pressure sensor aperture 1916. Optionally, a stop 1915, 1919 helps to assure proper placement of the sensor, for example, a mechanical pressure sensor such as that described in relation to pressure sensing socket 1918.

In some embodiments of the invention, a tip assembly 1800 comprises a relatively hard shell 1801, with a softer mounting portion 1805. Optionally, mounting portion 1805 comprises an insert into a receiving aperture 1801A of hard shell 1801. Potentially, a soft insert/hard shell configuration provides an advantage by allowing the material to be selected according to the functions performed by each portion 1801, 1805. For example, a hard shell potentially provides greater dimensional stability to the tip adaptor overall. Potentially, this encourages the tip to slide over rather than deformingly embed within intestinal tissue that it encounters, an advantage for navigation and/or safety, for example. Potentially, a soft insert provides an advantage for resisting the tendency of tubes inserted to thereto from being pried out of position upon application of bending forces to the cleaning assembly (if made to a softness similar to the tubes 110, the insert bends to a greater degree along with the tubes themselves as they are flexed).

Another potential advantage of the two-hardness construction is to enhance elastic friction fitting of the various small tubes which connect to the tip; for example, by making sockets 1912, 1914, 1902, and/or 1918 slightly smaller than the tubes which are pressingly fitted into them. Potentially, the hard shell provides an advantage for allowing a relatively lower friction material (of the body itself, and/or of a coating) to be used for regions of the tip liable to contact the intestinal wall 1. Optionally, both components are made of polyurethane (of appropriately differing hardness). Optionally, the outer component is coated, for example with a friction reducing material such as Parylene C, Teflon, or another low-friction material.

In some embodiments, the hardness of the internal tip portion 1805 is, for example, within the range of 25-40 Shore A, 30-50 Shore A, 35-55 Shore A, or within another range of softness having the same, larger, smaller, and/or intermediate bounds.

In some embodiments, the hardness of the external tip portion 1801 is, for example, within the range of 40-60 Shore A, 60-80 Shore A, 70-90 Shore A, or within another range of softness having the same, larger, smaller, and/or intermediate bounds.

In some embodiments of the invention, a tip assembly 1800 comprises a relatively soft shell 1801, with a harder mounting portion 1805. Optionally, mounting portion 1805 comprises an insert into a receiving aperture 1801A of soft shell 1801. Potentially, a soft shell/hard insert configuration provides an advantage by allowing the material to be selected according to the functions performed by each portion 1801, 1805, with a different emphasis than described for the soft insert/hard shell embodiments hereinabove.

For example, a hard insert potentially provides dimensional stability to the tip adaptor interfaces with tubing connectors such as sockets 1902, 1912, 1914, 1918, and/or to the dimensions of apertures such as apertures 1920 which optionally direct and/or shape fluid jets. Potentially, a hard insert is manufacturable to closer tolerances than a soft insert, for example to achieve tighter fitting, and/or closer control of jet aperture characteristics. During storage, a hard insert potentially resists creep, sagging, or other deformation which could potentially affect performance. During use, dimensional stability potentially prevents forces exerted on the tip from distorting, dislodging and/or loosening socket-tube connections. Potentially, dimensional stability of fluid jet apertures prevents distortion which affects the aiming and/or jet forming characteristics of the aperture.

In some embodiments, a soft shell protects tissue from encounters with hard portions of the tip. In general, providing a soft "skin" for the shell 1801 potentially helps to prevent damaging effects of poking and/or scraping. For example, a soft construction for shell 1801 softens the edges around apertures such as colonoscope mounting lumen 1903, irrigation outlet 1920, and/or evacuation socket aperture 1923. A soft shell 1801 also potentially distributes contact forces at other parts of the tip assembly 1800, for example at outer corners and/or curves.

In some embodiments, one or more compressible chambers and/or hollows are provided which potentially augment the protective effects of a soft shell 1801. For example, antechamber 1910 is optionally manufactured of material of sufficient softness and/or wall thinness such that the hollow it defines is easily collapsible upon encountering contact forces.

In some embodiments, the antechamber 1910 is flexible enough to allow elastic collapse with light pressure (for example, a pressure of between 1-10 Newtons, or another greater or smaller pressure). The collapse pressure is optionally chosen to be light enough that it is unlikely to damage the colon and/or at a level which is ordinarily encountered during advance within the colon. Optionally, collapsing pressure is deliberately brought to bear on the antechamber 1910 during use. Potentially, the collapsing action allows mechanically clearance of blockages within the chamber, and/or at one of the entrances to/exits from the chamber.

Additionally or alternatively, shell 1801 is manufactured with other hollows within its structure. For example, the wall thickness of a shell region 1803 comprises hollow regions defined by relatively thin membranes of soft material (in a honeycomb formation, for example). The chambers are optionally sealed or left unsealed on at least one side.

In some embodiments, the regions of soft and hard material are provided in different regions than shown in the figures. For example, the soft material of shell 1801 optionally comprises nearly all of the material volume of a tip assembly 1800, with the dimensionally stable hard material being provided as one or more inserts (for example, a plurality of tubular inserts) to define structures such as sockets and/or apertures. Some embodiments of the invention comprise another alternative construction; for example, a plurality of alternating and/or intermingled soft and hard layers and/or partial or segmented shells. In some embodiments, at least a portion of the relative advantages of each type of two-hardness construction (soft inside, hard outside; hard inside, soft outside) is potentially obtained by such construction variations. For example, hard sockets and/or jet apertures (potentially providing dimensional stability for connection/jet formation) are optionally embedded in a softer matrix (potentially allowing parts to move with respect to one another without being dislodged thereby); the softer matrix is optionally embedded in a harder outer part (optionally helping to preserve overall strength and/or shape of the adaptor), and the harder outer part itself is optionally provided with soft regions which act as force-absorbing and/or edge shielding bumpers.

Optionally, one or both of the soft and hard components are made of polyurethane (of appropriately differing hardness). Optionally, the outer component is coated, for example with a friction reducing material such as Parylene C, Teflon, or another low-friction material.

In some embodiments, the hardness of the shell portion 1801 is, for example, within the range of 25-40 Shore A, 30-50 Shore A, 35-55 Shore A, or within another range of softness having the same, larger, smaller, and/or intermediate bounds. In some embodiments, the hardness of the insert tip portion 1805 is, for example, within the range of 40-60 Shore A, 60-80 Shore A, 70-90 Shore A, or within another range of softness having the same, larger, smaller, and/or intermediate bounds.

Figure 20:
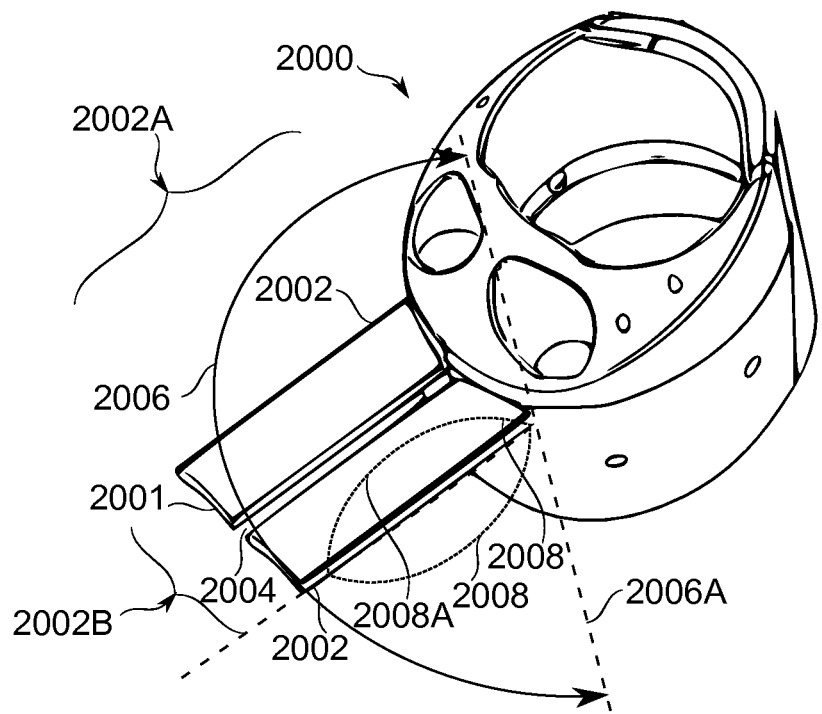
FIG. 20 schematically illustrates a tip adaptor comprising a flexible wall guard, according to some exemplary embodiments of the invention.

Reference is now made to FIG. 20, which schematically illustrates a tip adaptor 2000 comprising a flexible wall guard 2001, according to some exemplary embodiments of the invention.

In some embodiments of the invention, a tip adaptor 2000 comprises a flexible wall guard 2001, which acts as a spacing, positioning and/or aiming aid during colon cleaning operations.

In some embodiments, the wall guard 2001 comprises one or more flexible members 2002 attached at one end to the tip body, and having a length 2002A of about, for example, 10-15 mm, 12-18 mm, 15-20 mm, 18-24 mm, or another range of lengths having the same, larger, smaller, and/or intermediate bounds. In some embodiments, the total width 2002B of the wall guard 2001 is within the range of about, for example, 5-7 mm, 6-9 mm, 8-12 mm, 9-14 mm, or another range having the same, larger, smaller, and/or intermediate bounds. Optionally, a plurality of flexible members are separated by a gap 2004; for example, a gap of 1-2 mm or another gap width.

In some embodiments, the members of wall guard 2001 are sufficiently flexible to fully bend through a range 2006 of about 180° or more. In some embodiments, the maximum bending range is, for example, about 150°, 160°, 170°, 180°, 190°, or another larger, smaller, or intermediate maximum range. In some embodiments, the wall additionally or alternatively is configured to flex along its length, for example through a flexing range 2008. In some embodiments, the maximal flexing range is optionally from about doubled over (180°), or a smaller range such as about 90°, about 45°, or another maximum range which is larger, smaller, or intermediate. A paired-rectangle "rabbit ear" configuration is shown in FIG. 20; however, it is to be understood that other shapes are also embodiments of the invention—for example, triangular, oval, semi-circular, or another shape. In some embodiments of the invention, the thickness of the wall guard members is varied according to distance from the tip, in order to encourage more or less bending along the length, according to the specific bending characteristics desired. The hardness of the wall guard members 2002 (which comprise, for example, polyurethane or another rubber polymer) are, for example, about 20-30 Shore A, 30-45 Shore A, 40-55 Shore A, or within another range of hardness having the same, larger, smaller, and/or intermediate bounds. It is to be understood that the wall guard 2001 is optionally provided with any of the cleaning system tip embodiments described herein. Optionally, the wall guard 2001 is integrally formed with a soft outer shell such as shell 1801, optionally surrounding an insert such as mounting portion 1805.

Figure 22:
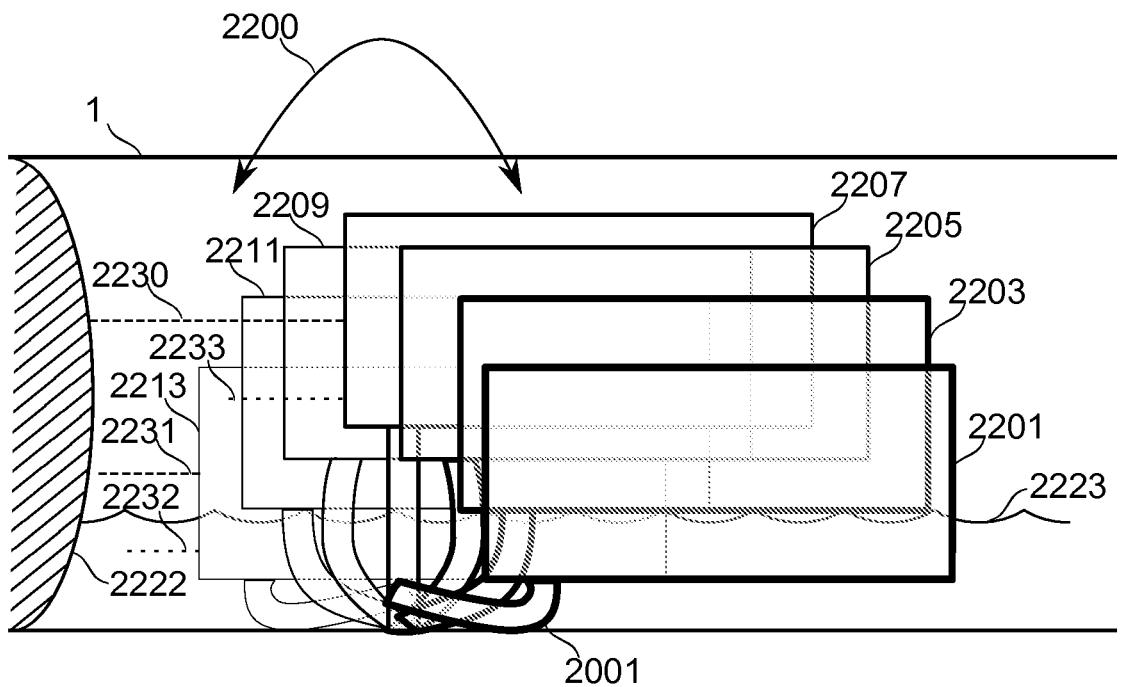
FIG. 22 illustrates positions of a cleaning system distal region (comprising for example, an adaptor tip), in relation to an intestinal wall and a flexible wall guard.

Reference is now made to FIG. 22, which illustrates positions 2201, 2203, 2205, 2207, 2209, 2211, 2213 of a cleaning system distal region (comprising for example, an adaptor tip 2100), in relation to an intestinal wall 1 and a flexible wall guard 2001.

Wall guard 2001 provides a potential advantage by acting as a soft (atraumatic) stand-off from the intestinal wall through which a cleaning system tip 2000 navigates. Potentially, this reduces instances of suction attachment to the intestinal wall.

Nevertheless, the wall guard 2001 is optionally sufficiently soft that it tends to elastically collapse upon exercise of sufficient force, for example, upon encountering a restriction in the colon (for example, a constriction at a colon segment boundary), such that navigation through the restriction is relatively unimpeded. Positions 2200 and 2213 show examples of the wall collapsed in a distal- and proximal-pointing orientation, respectively. In some embodiments, the members 2002 are provided as balloons inflatable through fluid communication with a pressure source (such as an irrigation tube 101, or another tube which is specially provided for wall inflation). This optionally allows control of wall stiffness according to the current navigational requirements.

In some embodiments of the invention, the wall guard 2001 serves as a device that helps to position the tip radially within the colon. For example: as the tip is advanced from position 2207, wall guard members 2002 tend to flex backward and toward the tip body to a position approximating that of line 2006A and/or position 2213, such that the tip can more closely approach the intestinal wall 1. However, with a slight backward pull, the members 2002 tend to straighten, for example, toward position 2008A and/or 2207. This potentially pushes the tip away from the wall. An optional alternative maneuver is to bend the wall forward by withdrawing the tip proximally; from this position, advancing rises up on the walls (sequence of positions 2201, 2203, 2205, 2207, for example). By this means, different radial positions for the tip are selectable, which potentially allows selection of the position at which jets are aimed when irrigation fluid is supplied—for example the difference in position between jet aiming directions 2230 and 2231.

Additionally or alternatively, the tip is repositioned by the wall guard to a radial position better suited to further advancement—for example, nearer to an aperture region in an intestinal restriction. Optionally, alternate short backward and forward movements of the tip region (for example, between positions 2201 and 2213) result in the tip "scanning" within the lumen and toward and away from the intestinal wall 1 (paralleling, for example, a path like 2200). This potentially distributes the energy of irrigation jets over a cleaning target 2222, and/or allows selection of a position suited for draining fluid from the intestine relative to a waste level 2223 (allowing, for example, positioning an evacuation intake zone between levels 2232 and 2233). An evacuation position is optionally selected, for example, such that the evacuation access apertures 1921 are immersed, but the evacuation antechamber aperture 1910A remains clear of fluid.

Optionally, rotation of the device puts more force on one of the wall members 2002 than on the other, as another method of guard-wall mediated steering. Optionally, the device is deliberately rotated by about 90° to move the guard wall out of the way and bring a portion of an evacuation access aperture nearer to a lower intestinal wall 1 portion, such that small amounts of remaining fluid can be evacuated.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or to identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A tip adaptor of a colon cleaning system for use with a probe portion of a colonoscope wherein:
   the tip adaptor comprises a shell and an insert having a portion inserted to the shell;
   said shell has:
      a hollow region sized to fittingly accommodate said insert, wherein the material of the shell fully circumferentially surrounds the insert received in said hollow region; and
      a mounting lumen, radially spaced from the hollow region, and comprising at least one aperture sized to fittingly receive and fixedly engage a distal end of the probe portion therein;
   the probe portion maintains fluid communication with a body cavity through the aperture;
   the insert portion inserted to the shell comprises a plurality of sockets, each fittingly accommodating a distal end of one or more respective fluid transport tubes;
   the insert comprises a first component and the shell comprises a second different component; and
   wherein said shell is elastic enough to deform around said insert in response to external force, and said insert is rigid relative to said shell.

2. The tip adaptor of claim 1, wherein in response to external force, the rigid insert remains substantially undeformed.

3. The tip adaptor of claim 1, wherein an aperture of at least one of said plurality of sockets is a suction intake aperture.

4. The tip adaptor of claim 1, wherein said hollow region is sufficiently flexible to elastically collapse upon being pressed from within against a portion of colon wall, the collapse occurring at a force below 10 Newtons of force.

5. The tip adaptor of claim 1, wherein an aperture of at least one of said plurality of sockets is an irrigation aperture.

6. The tip adaptor of claim 5, wherein the irrigation aperture is shaped to form fluid into a jet upon the supply of fluid therethrough.

7. The tip adaptor of claim 1, wherein the insert is attached to a distal end of an evacuation channel sized for insertion to a distal segment of a colon.

8. The tip adaptor of claim 7, wherein said tip adaptor is attached so that it is positioned for suctioning waste to said evacuation channel from said distal segment of a colon when inserted therein.

9. The tip adaptor of claim 2, comprising a colon spacer integrally formed with the shell, attached to a circumference of the tip adaptor and extending radially therefrom;
   the colon spacer being sufficiently flexible that it collapses upon receiving pressure due to forward motion of the tip adaptor into a radially restricted region of colon.

10. The tip adaptor of claim 1, wherein the shell surrounds the probe portion of the colonoscope and the insert so that the probe portion of the colonoscope and insert are co-located in said shell.

11. The tip adaptor of claim 2, wherein the plurality of sockets are made dimensionally stable by the harder undeformed insert portion.

12. The tip adaptor of claim 1, wherein the tip adaptor, including both the shell and the insert, is removably attachable to the probe portion of the colonoscope.

13. The tip adaptor of claim 1, comprising an evacuation antechamber having an open region fluidly interconnecting at least one socket of the insert portion with at least one aperture positioned in a recessed location sheltered from intestinal wall suction contact when the device is within an intestine, and at least one additional vent aperture of the evacuation antechamber.

14. The tip adaptor of claim 1, wherein the material of said shell moves about 0.1 mm in response to between 1-10 Newtons of force.

15. The tip adaptor of claim 1, wherein said shell is soft enough to distribute forces encountered by said tip adaptor, to prevent focusing force to a small region of tissue being contacted by said tip adaptor.

* * * * *